United States Patent
Leana et al.

(10) Patent No.: US 9,522,203 B2
(45) Date of Patent: Dec. 20, 2016

(54) STABILIZED CHLORINE DIOXIDE FOR CONTAMINATION CONTROL IN ZYMOMONAS FERMENTATION

(71) Applicant: E I DU PONT DE NEMOURS AND COMPANY, Wilmington, DE (US)

(72) Inventors: Maria C Leana, Hockessin, DE (US); Brian G Lefebvre, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/468,364

(22) Filed: Aug. 26, 2014

(65) Prior Publication Data
US 2015/0359916 A1 Dec. 17, 2015

Related U.S. Application Data

(62) Division of application No. 13/721,103, filed on Dec. 20, 2012, now Pat. No. 8,846,357.

(51) Int. Cl.
| | |
|---|---|
| A61L 2/18 | (2006.01) |
| C12H 1/00 | (2006.01) |
| C08H 8/00 | (2010.01) |
| C12N 1/22 | (2006.01) |
| C12P 7/06 | (2006.01) |
| C12N 1/20 | (2006.01) |

(Continued)

(52) U.S. Cl.
CPC . *A61L 2/18* (2013.01); *C08H 8/00* (2013.01); *C08L 97/02* (2013.01); *C12H 1/00* (2013.01); *C12N 1/20* (2013.01); *C12N 1/22* (2013.01);

*C12N 1/36* (2013.01); *C12N 9/2437* (2013.01); *C12P 7/065* (2013.01); *C12P 7/10* (2013.01); *C12N 2500/05* (2013.01); *C12Y 302/01004* (2013.01); *Y02E 50/16* (2013.01); *Y02E 50/17* (2013.01)

(58) Field of Classification Search
CPC ........................................................ A61L 2/18
See application file for complete search history.

(56) References Cited

U.S. PATENT DOCUMENTS

| | | |
|---|---|---|
| 3,585,147 A | 6/1971 | Gordon |
| 3,591,515 A | 7/1971 | Lovely |

(Continued)

FOREIGN PATENT DOCUMENTS

| | | | | |
|---|---|---|---|---|
| JP | 2010136702 A | * | 6/2010 | ............... C12P 7/06 |
| WO | 2007097874 A1 | | 8/2007 | |

(Continued)

OTHER PUBLICATIONS

Machine translation of specification of JP 2010-136702 A, printed on Apr. 18, 2016.*

(Continued)

*Primary Examiner* — Rosanne Kosson

(57) ABSTRACT

Though chlorine dioxide is generally used to control bacterial contamination, a method was developed which allows the use of stabilized chlorine dioxide (SCD) for controlling contamination during fermentation that uses the bacteria *Zymomonas* as the biocatalyst, even though *Zymomonas* is sensitive to chlorine dioxide. Parameters were identified for inoculating a composition for fermentation with *Zymomonas* cells after a time period has elapsed following SCD addition.

10 Claims, 10 Drawing Sheets

(51) Int. Cl.
*C12N 1/36* (2006.01)
*C12P 7/10* (2006.01)
*C08L 97/02* (2006.01)
*C12N 9/42* (2006.01)

(56) References Cited

U.S. PATENT DOCUMENTS

| | | | |
|---|---|---|---|
| 4,885,241 | A | 12/1989 | Millichip |
| 4,985,355 | A | 1/1991 | Millichip |
| 6,419,788 | B1 | 7/2002 | Wingerson |
| 7,629,156 | B2 | 12/2009 | Viitanen et al. |
| 7,741,084 | B2 | 6/2010 | Viitanen et al. |
| 7,741,119 | B2 | 6/2010 | Viitanen et al. |
| 7,781,191 | B2 | 8/2010 | Dunson, Jr. et al. |
| 7,803,623 | B2 | 9/2010 | Caimi et al. |
| 7,897,396 | B2 | 3/2011 | Caimi et al. |
| 7,910,338 | B2 | 3/2011 | Hennessey et al. |
| 7,932,063 | B2 | 4/2011 | Dunson, Jr. et al. |
| 7,989,206 | B2 | 8/2011 | Viitanen et al. |
| 7,998,713 | B2 | 8/2011 | Dunson, Jr. et al. |
| 7,998,722 | B2 | 8/2011 | Viitanen et al. |
| 2009/0042276 | A1 | 2/2009 | Maye |
| 2009/0053770 | A1 | 2/2009 | Hennessey et al. |
| 2011/0014670 | A1 | 1/2011 | Caimi et al. |
| 2011/0143408 | A1 | 6/2011 | Yang |
| 2011/0207192 | A1 | 8/2011 | Pigeau et al. |
| 2011/0318801 | A1 | 12/2011 | Kahsay et al. |
| 2011/0318803 | A1 | 12/2011 | Hitz et al. |
| 2012/0156746 | A1 | 6/2012 | Caimi et al. |
| 2012/0329114 | A1 | 12/2012 | Caimi et al. |

FOREIGN PATENT DOCUMENTS

| | | |
|---|---|---|
| WO | 2007145857 A1 | 12/2007 |
| WO | 2007149450 A2 | 12/2007 |
| WO | 2011038317 A1 | 3/2011 |

OTHER PUBLICATIONS

English bibliographic information of JP 2010-136702 A, from East, printed on Apr. 18, 2016.*

English bibliographic information of JP 2010-136702 A, from JPO, printed on Apr. 18, 2016.*

Day, W. H. et al., Antibiotics as Contamination-Control Agents in Grain Alcohol Fermentations, Agricultural and Food Chemistry, Mar. 3, 1954, pp. 252-258, vol. 2, No. 5.

Hynes, SH et al., Use of virginiamycin to control the growth of lactic acid bacteria during alcohol fermentation, Journal of Industrial Microbiology & Biotechnology, 1997, pp. 284-291, vol. 18.

Bischoff, Kenneth M. et al., Modeling Bacterial Contamination of Fuel Ethanol Fermentation, Biotechnology and Bioengineering, May 1, 2009, pp. 117-122, vol. 103, No. 1.

Fatka, Jacqui, Ethanol additive safer, effective, Feedstuffs, Nov. 3, 2008.

Meneghin, Silvana Perissatto et al., Chlorine dioxide against bacteria and yeasts from the alcoholic fermentation, Brazilian Journal of Microbiology, Apr./Jun. 2008, pp. 337-343, vol. 39, No. 2.

Agrawal, Renu et al., Role of Antimicrobial Agents in Simultaneous Saccharification and Ferrnantation of Paddy Malt Mash to Ethanol by Mixed Cultures of *Saccharomyces cerevisiae* PH03 and *Zymomonas Mobilis* ZM4, Biotechnology Letters, Jun. 1996, pp. 673-678, vol. 18, No. 6.

Muthaiyan, Arunachalam et al., Antimicrobial strategies for limiting bacterial contaminants in fuel bioethanol fermentations, Progress in Energy and Combustion Science, 2011, pp. 351-370, vol. 37, No. 3.

Association of Cereal Research, Review and Summaries 2012; 8. European Technology Meeting, Production and Certfication Bioethanol production in Europe, Apr. 17, 2012, pp. 1-15.

Lau, Ming W. et al., Comparing the fermentation performance of *Escherichia coli* KO11, *Saccharomyces cerevisiae* 424A(LNH-ST) and Zymomonas mobilis AX 101 for cellulosic ethanol production, Biotechnology for Biofuels, 2010, pp. 1-10, 3;11.

International Search Report—International Application No. PCT/US2013/074235—Mailed Mar. 12, 2014.

* cited by examiner

STABILIZED CHLORINE DIOXIDE FOR CONTAMINATION CONTROL IN ZYMOMONAS FERMENTATION

FIELD OF THE INVENTION

The invention relates to the fields of microbiology and fermentation. More specifically, methods were developed for controlling bacterial contamination in fermentations using stabilized chlorine dioxide when *Zymomonas* is used as the biocatalyst in a hydrolysate medium.

BACKGROUND OF THE INVENTION

Fuel ethanol produced from renewable resources is one of the long-term solutions to global fossil fuel shortages, rising energy costs, and global warming effects related to increased atmospheric carbon dioxide. Fuel ethanol from renewable resources is produced by fermentation of sugars using a biocatalyst. Currently yeast is the biocatalyst most widely used for ethanol production. Fermentable sugars are most typically obtained from processed biomaterials including corn grain, sugarbeets, and sugar cane. An alternative abundant biomaterial sugar source is cellulosic or lignocellulosic biomass. Methods are being developed for processing of cellulosic and lignocellulosic biomass to produce fermentable sugars using physical, chemical, and/or enzymatic treatments.

It is difficult to maintain sterility in a large scale fermentation process, particularly when biomaterial is used as a carbohydrate source. Large scale ferrmentation processes are typically contaminated with bacteria that may come from the processed biomaterial, equipment, process water or other sources. Typically contaminating bacteria are lactic acid bacteria (LAB) such as *Lactobacillus* species. Contaminating bacteria reduce fermentation product yield by utilizing sugars and reducing effectiveness of the primary product biocatalyst. Contaminating bacteria produce undesired products such as acetic and lactic acid which increase stress conditions in a culture leading to poorer growth of the biocatalyst and/or lower production of the biocatalyst product.

Contaminating bacteria, predominantly lactic acid bacteria, have been a problem in fermentations that use yeast as the biocatalyst, typically with mash or molasses used as the carbohydrate source for ethanol production for either fuel or brewing. Due to differential sensitivities of yeast and contaminating bacteria to some antimicrobials, a number of antimicrobials can be used to control bacteria in yeast fermentations. Antimicrobials successfully used in yeast fermentations to control LAB contamination include penicillin (Day et al. (1954) Agricultural and Food Chemistry 2:252-258), virginiamycin (Hynes et al. (1997) J. of Industrial Microbiology & Biotechnology 18:284-291; Bischoff et al. (2009) Biotechnology and Bioengineering 103:117-122; WO2007145857), hop acids (US20090042276), erythromycin, tylosin, tetracycline and chlorine dioxide (FermaSure®; Dupont Company, Wilmington Del.; Fatka, Feedstuffs (Nov. 3, 2008) p 18).

Treating an aqueous stream comprising a fermentable carbohydrate and yeast with $ClO_2$ gas to reduce undesirable microorganism concentration is disclosed in WO 2007/097874. Treating a yeast slurry from a yeast ethanol production process with chlorine dioxide to destroy microbial contaminants while maintaining yeast viability is disclosed in US 2009/0061490. A fermentation process comprising a fermentable sugar, an inoculate (yeast), and stabilized chlorine dioxide which is used to substantially prevent growth of bacteria, is disclosed in WO2007/149450. Use of stabilized chlorine dioxide to preserve a carbohydrate solution against microorganisms is disclosed in WO2011038317.

*Zymomonas* is being developed as an effective biocatalyst for producing ethanol by engineering strain improvements including utilization of xylose and arabinose in addition to glucose, and inactivating competing metabolic pathways. In addition, *Zymomonas* has been adapted for use in hydrolysate fermentation medium by increasing tolerance to inhibitors present in cellulosic biomass hydrolysate. However, using *Zymomonas* as a biocatalyst for ethanol fermentation presents additional challenges in contamination control since this biocatalyst is a bacterium, as are the predominant contaminants. Thus differential activity of antimicrobials to yeast and bacteria cannot be exploited as in processes that produce ethanol using a yeast biocatalyst.

There remains a need for methods to control bacterial contaminants in fermentations that use a bacterial *Zymomonas* biocatalyst.

SUMMARY OF THE INVENTION

The invention provides compositions and methods for controlling bacterial contamination in fermentations where *Zymomonas* is the biocatalyst.

Accordingly, the invention provides a fermentation method for controlling bacterial contamination in a fermentation process comprising a *Zymomonas* biocatalyst comprising:
  a) providing a growth medium having the potential for being contaminated by a bacterial species;
  b) adding an effective amount of stabilized chlorine dioxide to the growth medium of (a) forming a stabilized chlorine dioxide mixture wherein the temperature of the stabilized chlorine dioxide mixture is greater than about 33° C.;
  c) inoculating the mixture of b) with *Zymomonas* cells at a temperature suitable for *Zymomonas* cells to produce an inoculated broth; and
  d) fermenting the inoculated broth under conditions suitable for growth of the *Zymomonas* cells;
wherein bacterial contamination is controlled during fermentation.

In one embodiment the *Zymomonas* is an ethanologen and ethanol is produced in the fermentation broth of the method.

In another embodiment the invention provides a fermentation medium mixture composition comprising:
  a) cellulosic biomass hydrolysate fermentation medium; and
  b) stabilized chlorine dioxide.

In yet another embodiment the invention provides a saccharification reaction slurry mixture composition comprising:
  a) cellulosic biomass;
  b) at least one cellulase enzyme; and
  c) stabilized chlorine dioxide.

In another aspect of the invention a fermentation method for controlling bacterial contamination in a fermentation process comprising a *Zymomonas* biocatalyst is provided comprising the steps of:
  a) providing a seed medium lacking cellulosic biomass hydrolysate selected from the group consisting of: i) defined medium, ii) medium containing a non-cellulosic biomaterial sugar source, and iii) clarified cellulosic biomass hydrolysate;

b) inoculating the seed medium of a) with *Zymomonas* ethanologen cells to form a seed culture;

c) growing the *Zymomonas* cells in the seed culture of b);

d) Inoculating a saccharification reaction slurry with the seed culture of c) to produce an inoculated saccharification slurry;

e) mixing the inoculated saccharification slurry with a fermentation medium to produce a fermentation beer; and f) growing the *Zymomonas* ethanologen cells in the fermentation beer under conditions whereby ethanol is produced;

wherein:
stabilized chlorine dioxide is added to at least one of i) the seed medium of step a); ii) the saccharification reaction slurry of step d) or iii) the fermentation medium of step e): and wherein:
if the stabilized chlorine dioxide is added to the seed medium of step a) the seed medium is maintained at a temperature of at least about 33° C. for at least about 6 hours prior to inoculation with the *Zymomonas* ethanologen; and wherein:
if the stabilized chlorine dioxide is added to the saccharification reaction slurry of step d) the saccharification reaction slurry is maintained at a temperature of at least about 33° C. for at least about 8 hours prior to inoculation with the seed culture; and wherein:
if the stabilized chlorine dioxide is added to the fermentation medium of step e) the fermentation medium is maintained at a temperature of at least about 33° C. for at least about 8 hours prior to the mixing with the saccharification reaction slurry; and wherein:
any one of the seed culture, the inoculated saccharification slurry or the fermentation beer comprising *Zymomonas* cells contains less than about 5 g/L of lactic acid during the period of the growth of the *Zymomonas* cells.

DETAILED DESCRIPTION

Figure 1:
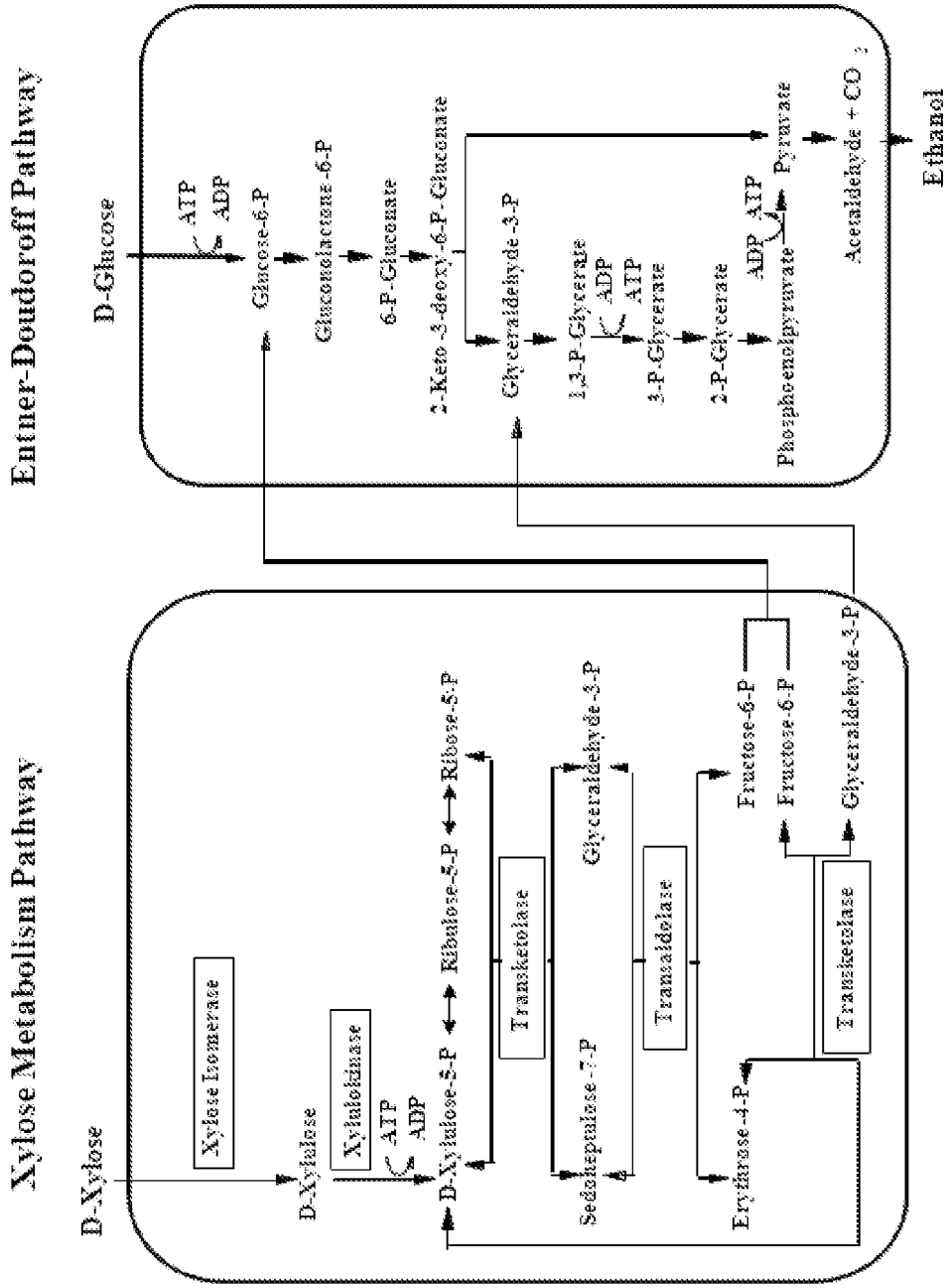
FIG. 1 shows a diagram of the ethanol fermentation pathway in *Zymomonas* engineered for xylose utilization.

The invention relates to the use of stabilized chlorine dioxide (SCD) as an antibacterial agent to control contaminating bacteria in fermentations that use *Zymomonas* as the biocatalyst, such as for production of ethanol. Contaminating bacteria present in a carbohydrate solution or slurry are controlled by SCD, however SCD is found herein to be detrimental to growth and production of *Zymomonas* cells. A process for controlling contamination during *Zymomonas* fermentation that makes use of stabilized chlorine dioxide was developed. In particular, stabilized chlorine dioxide is added to a growth medium (which may include a fermentation medium or saccharification reaction slurry) that is maintained at a temperature that is greater than 33° C. for a period of time prior to reducing the temperature to a temperature that is suitable for fermentation, if needed, and inoculating with *Zymomonas* cells forming a fermentation broth. Reducing the temperature is needed if the temperature at which the SCD mixture is maintained is higher than is suitable for fermentation. By allowing a time period at elevated temperature to elapse between adding SCD and inoculating with *Zymomonas* cells, the detrimental effect of SCD is alleviated such that the *Zymomonas* cells can effectively grow and produce ethanol. One factor affecting the length of time required is the type of growth medium or fermentation medium to which the SCD is added, or whether SCD is added to a saccharification reaction slurry, and the type of the slurry.

This process may be used for efficient production of ethanol from renewable resources for use as a fuel additive to address shortages in fossil fuels, reduce energy costs and impact global warming.

The following definitions and abbreviations are to be use for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "ethanologen" refers to an organism that produces ethanol through metabolism of carbohydrate sources.

The term "fermentable sugar(s)" refers to oligosaccharides and monosaccharides that can be used as a carbon source by a microorganism in a fermentation process The term "simultaneous saccharification and fermentation (SSF)" refers to a process wherein biomass is saccharified and the fermentable sugars produced from saccharification are used by a biocatalyst to produce a product all at the same time, typically in the same reaction vessel.

The term "cellulosic" refers to a composition comprising cellulose and additional components that may include hemicellulose and lignin.

The term "lignocellulosic" refers to a composition comprising both lignin and cellulose. Lignocellulosic material may also comprise hemicellulose.

The term "saccharification" refers to the production of fermentable sugars from polysaccharides.

The term "biomaterial" refers to any biologically derived material that is a source of carbohydrates that may be used in fermentation by a biocatalyst. Biomaterial includes cellulosic biomass as well as other plant materials and plant-derived materials used as carbohydrate sources such as grains, mash, molasses, and raw juice (such as from sugar beets and sugar cane).

The term "slurry" refers to a mixture of insoluble material and a liquid.

The term "cellulosic biomass saccharification reaction slurry" refers to a mixture comprising cellulosic biomass and at least one cellulase enzyme wherein cellulose and other polysaccharides are hydrolyzed to produce fermentable sugars during the reaction. The biomass may also be pretreated prior to including in a saccharification reaction slurry. The mixture contains insoluble material and a liquid and thus is a slurry.

The term "pretreated biomass" means biomass that has been subjected to pretreatment prior to saccharification.

The term "cellulosic biomass" refers to any cellulosic or lignocellulosic material and includes materials comprising cellulose, and optionally further comprising hemicellulose, lignin, starch, oligosaccharides and/or monosaccharides. Cellulosic biomass may also comprise additional components, such as protein and/or lipid. Cellulosic biomass may be derived from a single source, or can comprise a mixture derived from more than one source; for example, cellulosic biomass could comprise a mixture of corn cobs and corn stover, or a mixture of grass and leaves. Cellulosic biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat, wheat straw, barley straw, hay, rice straw, switchgrass, waste paper, sugar cane bagasse, sorghum or soy cellulosic plant material, cellulosic components obtained from milling of grains, trees, branches, roots, leaves, wood chips, sawdust, shrubs and bushes (woody plant cellulosic components), vegetables, fruits, flowers and animal manure.

The term "cellulosic biomass hydrolysate" refers to the product resulting from saccharification of cellulosic or lignocellulosic biomass. The biomass may also be pretreated prior to saccharification. Cellulosic biomass hydrolysate is a product containing biomass solids.

The term "clarified cellulosic biomass hydrolysate" or "clear cellulosic biomass hydrolysate" refers to a cellulosic biomass hydrolysate which has been processed to remove solids and is not considered to be a cellulosic biomass hydrolysate. In addition The term "saccharification enzyme" refers to an enzyme that can catalyze conversion of a component of biomass to fermentable sugars. Typically the enzyme is more effective when the biomass is pretreated.

The term "substantial contamination" refers to a level of lactic acid bacteria contamination in a fermentation broth that would produce more than about 5 g/L of lactic acid if the fermentation broth were incubated without an antimicrobial for about 40 hours.

The term "lactic acid bacteria" refers to bacteria that produce lactic acid as a major metabolic end-product of carbohydrate fermentation. The lactic acid bacteria (LAB) are gram positive bacteria belonging to the order Lactobacillales, and include for example the genera *Lactobacillus, Leuconostoc, Lactococcus, Pediococcus, Streptococcus*, and *Enterococcus*.

The term "growth medium" means a liquid medium capable of supporting the growth of a *Zymomonas* biocatalyst. Typical growth media useful in the present invention include fermentation medium and saccharification reaction slurries which may comprise cellulosic biomass hydorlysate.

The term "fermentation medium" refers to a composition comprising components, such as nutrients, that support the growth of a microorganism used as a biocatalyst. Fermentation medium may be used in any size including small scale cultures and large scale production fermentations.

The term "fermentation broth" refers to a composition comprising fermentation medium and biocatalyst cells in which fermentation is occurring or has occurred. Depending on how long the biocatalyst has been grown in the fermentation broth, this broth may also include the product produced by the biocatalyst, such as ethanol.

The term "seed culture" is a culture of biocatalyst cells that is used to inoculate a larger volume of fermentation medium producing a fermentation broth. Typically a seed culture inoculum is about 0.01% to 20% v/v of the final volume of the fermentation broth.

The term "contamination" refers to the presence of microorganisms that are not intentionally introduced. Typically a desired biocatalyst is introduced into a growth medium producing a fermentation broth. Microorganisms present in the fermentation broth other than the introduced biocatalyst are considered to be contamination.

The present method provides for control of undesired bacteria in cultures where a *Zymomonas* bacterium is the biocatalyst, such as in fermentation for ethanol production. Undesired, contaminating bacteria are typically present in large scale processes, particularly when media contain processed biomaterial. Processed biomaterial used in media may include carbohydrate sources such as corn or wheat mash, sugar beet or sugar cane molasses, and lignocellulosic biomass hydrolysate. Contaminating bacteria may be introduced in a fermentation process from biomaterial, process equipment, inoculation cultures, process water, air, or other sources. Controlling contamination in a production fermentation typically allows the biocatalyst to grow and produce product to a higher level than that achieved in the presence of contaminating bacteria, providing a more efficient and economical fermentation process.

Though chlorine dioxide is generally used to control bacterial contamination, a method was developed which allows the use of stabilized chlorine dioxide (SCD) for controlling contamination during fermentation that uses the bacteria *Zymomonas* as the biocatalyst, even though *Zymomonas* is sensitive to chlorine dioxide. The predominant contaminating bacteria in large-scale fermentations using biomass-derived carbohydrate sources are lactic acid bacteria (LAB), such as strains of *Lactobacillus*. The contaminating bacteria compete with the biocatalyst for fermentable sugars and/or produce substances that are inhibitory to biocatalyst growth and production, such as lactic acid. In the present method SCD is added to a potentially contaminated fermentation medium or saccharification reaction slurry that is used to provide fermentable sugars for *Zymomonas* fermentation, a time period is allowed to pass, and then the SCD-containing mixture is inoculated with *Zymomonas* cells. It was found herein that though a level of SCD that is effective for controlling typical contaminating bacteria is also inhibitory to *Zymomonas* cell growth and ethanol production, if a time period is allowed to elapse between SCD addition and *Zymomonas* cell inoculation, the *Zymomonas* cells show levels of growth and product formation during fermentation comparable to those with no SCD treatment, while contamination remains low.

Stabilized Chlorine Dioxide

The term "stabilized chlorine dioxide" otherwise referred to herein as "SCD" means one or more chlorine dioxide-containing oxy-chlorine complexes, one or more chlorite-containing compounds, one or more other entities capable of forming chlorine dioxide when exposed to acid, and combinations thereof. Thus, stabilized chlorine dioxide comprises at least one of a chlorine dioxide-containing oxy-chlorine complex, a chlorite-containing compound, or an entity capable of forming chlorine dioxide in a liquid medium when exposed to acid.

Among the preferred chlorine dioxide-containing oxy-chlorine complexes is one selected from the group consisting of a complex of chlorine dioxide with carbonate, a complex of chlorine dioxide with bicarbonate, and mixtures thereof. Examples of chlorite-containing compounds include metal chlorites, and in particular alkali metal and alkaline earth metal chlorites. A specific example of a chlorite-containing compound that is useful as a chlorine dioxide precursor is sodium chlorite, which can be used as technical grade sodium chlorite.

SCD is preferably an aqueous solution of an alkali metal or alkaline earth metal chlorite, typically sodium chlorite ($NaClO_2$). Sodium chlorite in solution is generally stable at pH above 7, but releases the active chlorine dioxide ($ClO_2$), when the pH is lowered below neutral (pH 7). The rate of activation of SCD, that is, the rate at which the active $ClO_2$ is released from the stable form, increases as pH decreases.

The exact chemical composition of many of SCD compositions, and in particular, chlorine dioxide-containing oxy-chlorine complexes, is not completely understood. The manufacture or production of certain chlorine dioxide precursors is described by Gordon, U.S. Pat. No. 3,585,147 and Lovely, U.S. Pat. No. 3,591,515. Specific examples of commercially available and useful stabilized chlorine dioxide preparations include, for example, Anthium Dioxcide® and FermaSure® available from E. I. du Pont de Nemours and Company (Wilmington, Del.); and Oxine® and Purogene® available from Bio-fide International, Inc. (Norman, Okla.).

SCD may be provided as a solution of the one or more chlorine dioxide-containing oxy-chlorine complexes, one or more chlorite-containing compounds, one or more other entities capable of forming chlorine dioxide when exposed to acid, and combinations thereof. The solution provides SCD in a liquid at a predetermined concentration of actives as available chlorine dioxide ($ClO_2$). Preferably, the liquid medium has sufficient SCD to have an available chlorine dioxide concentration in the range of about 0.002% to about 40% by weight, preferably, in the range of about 2% to about 25% by weight, more preferably in the range of about 5% to about 15% by weight, based on the total weight of the liquid medium including the chlorine dioxide-containing oxy-chlorine complexes, chlorite-containing compounds, other entities capable of forming chlorine dioxide when exposed to acid, and combinations thereof.

SCD may be provided as a solid material, such as a composition comprising an alkali or alkaline earth metal chlorite powder, inert ingredients, and optionally dry activator such as a dry acid.

SCD may also be provided as a mixture (or slurry) comprising a saturated solution of alkali or alkaline earth metal chlorite powder and additional solid alkali or alkaline earth metal chlorite powder. Such slurries provide a liquid SCD with a higher active ingredient level than available in solution form.

In one embodiment SCD is stabilized alkali metal chlorite, more specifically sodium chlorite ($NaClO_2$) which is the most common and commercially available of the alkali metal chlorites. By stabilized alkali metal chlorite is meant a buffered solution of the chlorite at a pH above 7, preferably pH of 9-10. The solution typically comprises 5-22% w/w sodium chlorite in water, although the concentration of sodium chlorite may also be higher or lower.

Typically sodium chlorite is used as an aqueous solution comprising 5-22% by weight, based on solution weight of sodium chlorite in water. SCD concentrations may be described in terms of the concentration of chlorine dioxide ($ClO_2$) available when the chlorite is stoichiometrically converted to chlorine dioxide, "available $ClO_2$". The content of potential chlorine dioxide in 1 g of sodium chlorite is 0.597 g. Sodium chlorite solutions comprising 5-22% by weight of sodium chlorite thus contain 2.98-13.13% available chlorine dioxide. The generation of $ClO_2$ is illustrated by the following equation (1):

$$5NaClO_2 + 4H^+ \rightarrow ClO_2(g) + 2H_2O + Cl^- + 5Na^+ \qquad (1)$$

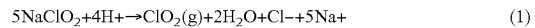

wherein one $NaClO_2$ molecule provides 0.8 $ClO_2$ molecules.

Concentrations of SCD are typically specified as the amount of chlorine dioxide that can be released from an SCD preparation upon complete activation by acid. This standardizes chlorine dioxide concentrations provided in different SCD preparations, used in compositions with different pHs.

When SCD is an aqueous solution of sodium chlorite, the SCD has a pH of greater than pH 7. Sodium chlorite solutions release the active chlorine dioxide as pH is lowered. The rate of chlorine dioxide release from SCD aqueous solutions increases as pH is reduced from pH of about 5 to 6.6, to 2.6. This rate may vary depending on several factors. For example, different $ClO_2$ precursors may release the $ClO_2$ at different rates at the same or similar pH. Other factors such as the buffering capacity of a solution may affect the rate of $ClO_2$ release from SCD solutions. These factors are well known to those skilled in the art.

Stabilized Chlorine Dioxide Mixtures for *Zymomonas* Fermentation

In the present method SCD is added to a composition for fermentation, such as a fermentation medium or saccharification reaction slurry, forming a stabilized chlorine dioxide mixture before the mixture is inoculated with a *Zymomonas* cell biocatalyst. Thus the SCD is added to fermentation medium or saccharification reaction slurry that is a source of fermentable sugars for *Zymomonas* cell fermentation. It is found herein that though *Zymomonas* cells are sensitive to chlorine dioxide, SCD may be added to compositions that are a source of sugars for *Zymomonas* cell fermentation if a time period elapses prior to inoculating with *Zymomonas* cells.

SCD may be added to growth medium of any type that supports growth and production during fermentation with *Zymomonas* as the biocatalyst. One skilled in the art will know how to prepare any of the described types of media in view of the information below. In one embodiment the growth medium is a defined medium. This medium contains typical purchased components including a carbohydrate source such as glucose, a source of amino acids and other nutrients such as yeast extract, and other components that may include trace elements, nitrogen, and phosphorus such as $KH_2PO_4$ and $MgSO_4$. Defined medium is often used for growing laboratory scale cultures as well as seed cultures that are used as inoculum for large scale fermentations.

In another embodiment the growth medium contains sugars obtained from non-cellulosic materials such as mash, raw juice, or molasses. These sugars are prepared from biomaterials such as cereal grains (such as corn, wheat, barley, and rye), and sugar crops such as sugar beets and sugar cane. Hydrolyzed mash used for fermentation is made from cereal grains typically by heating to a temperature above the gelatinization temperature, treating with alpha amylase to liquefy, and saccharifying using enzymes such as glucoamylase. Molasses or raw juice from sugar beets and sugar cane may be used as the sugar source in fermentation medium. This type of sugar source is a non-cellulosic biomaterial sugar source (cellulosic includes lignocellulosic), since the sugar source is primarily starch or sugar juice. This type of sugar source is typically used in seed cultures and in the production of ethanol using yeast as a biocatalyst, and in other non-cellulosic large scale fermentations.

Defined media and media having sugar from a non-cellulosic source lack cellulosic (including lignocellulosic) biomass hydrolysate. Additionally, media containing a sugar source that is obtained from cellulosic biomass, and is highly purified to remove other cellulosic components such as solids, is considered to be medium lacking cellulosic biomass hydrolysate. This type of medium contains a clarified cellulosic biomass hydrolysate.

In yet another embodiment the growth medium contains cellulosic biomass hydrolysate prepared from cellulosic (including lignocellulosic) biomaterials. Cellulosic biomass hydrolysate contains biomass solids. Cellulosic biomass hydrolysate is produced by saccharification of cellulosic (including lignocellulosic) biomass. Typically the biomass is pretreated prior to saccharification. Biomass may be treated by any method known by one skilled in the art to produce fermentable sugars in a hydrolysate. Typically the biomass is pretreated using physical and/or chemical treatments, and saccharified enzymatically. Physical and chemical treatments may include grinding, milling, cutting, base treatment such as with ammonia or NaOH, and/or acid treatment. Particularly useful is a low ammonia pretreatment where biomass is contacted with an aqueous solution comprising ammonia to form a biomass-aqueous ammonia mixture where the ammonia concentration is sufficient to maintain an alkaline pH of the biomass-aqueous ammonia mixture but is less than about 12 wt. % relative to dry weight of biomass, and where dry weight of biomass is at least about 15 wt % solids relative to the weight of the biomass-aqueous ammonia mixture, as disclosed in commonly owned U.S. Pat. No. 7,932,063, which is herein incorporated by reference.

Enzymatic saccharification of cellulosic or lignocellulosic biomass typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass components they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme. Many glycosyl hydrolase enzymes and compositions thereof that are useful for saccharification are disclosed in WO 2011/038019.

Saccharification enzymes may be obtained commercially. Such enzymes include, for example, Spezyme® CP cellulase, Multifect® xylanase, Accelerase® 1500, and Accellerase® DUET (Danisco U.S. Inc., Genencor International, Rochester, N.Y.), and Novosyme-188 (Novozymes, 2880 Bagsvaerd, Denmark). In addition, saccharification enzymes may be unpurified and provided as a cell extract or a whole cell preparation. The enzymes may be produced using recombinant microorganisms that have been engineered to express one or more saccharifying enzymes. For example, the H3A protein preparation used herein for saccharification of pretreated cellulosic biomass is an unpurified preparation of enzymes produced by a genetically engineered strain of *Trichoderma reesei*, which includes a combination of cellulases and hemicellulases and is described in WO 2011/038019, which is incorporated herein by reference.

Additional enzymes for saccharification include, for example, glycosyl hydrolases such as members of families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and the classification is available in the Carbohydrate-Active enzyme (CAZy) database (Cantarel et al. (2009) Nucleic Acids Res. 37 (Database issue):D233-238). Certain of these enzymes are able to act on various substrates and have demonstrated effecacy as saccharification enzymes. Glycoside hydrolase family 3 ("GH3") enzymes have a number of known activities, including, for example, β-glucosidase (EC:3.2.1.21); β-xylosidase (EC:3.2.1.37); N-acetyl β-glucosaminidase (EC:3.2.1.52); glucan β-1,3-glucosidase (EC:3.2.1.58); cellodextrinase (EC:3.2.1.74); exo-1,3-1,4-glucanase (EC: 3.2.1); and/or β-galactosidase (EC 3.2.1.23) activities. Glycoside hydrolase family 39 ("GH39") enzymes also have a number of known activities, including, for example, α-L-iduronidase (EC:3.2.1.76) and/or β-xylosidase (EC: 3.2.1.37) activities. Glycoside hydrolase family 43 ("GH43") enzymes have a number of known activities including, for example, L-α-arabinofuranosidase (EC 3.2.1.55); 3-xylosidase (EC 3.2.1.37); endoarabinanase (EC 3.2.1.99); and/or galactan 1,3-β-galactosidase (EC 3.2.1.145) activities. Glycoside hydrolase family 51 ("GH51") enzymes are known to have, for example, L-α-arabinofuranosidase (EC 3.2.1.55) and/or endoglucanase (EC 3.2.1.4) activities. Glycoside hydrolase family 10 ("GH10") have beendescribed in detail in Schmidt et al., 1999, Biochemistry 38:2403-2412 and Lo Leggio et al., 2001, FEBS Lett 509: 303-308) and the Glycoside hydrolase family 11 ("GH11") have been described in Hakouvainen et al., 1996, Biochemistry 35:9617-24.

The present fermentation medium mixture composition comprises cellulosic biomass hydrolysate fermentation medium and SCD. "Effective amounts" of SCD will be any amount that is effective to kill contaminating bacterial species without harming the biocatalyst. The effective amount of SCD will vary depending on the type of growth media used. In one embodiment the concentration of SCD is initially at least about 10 mg/kg, as described further below, with the amount of stabilized chlorine dioxide given in terms of the amount of chlorine dioxide that can be released upon complete activation of stabilized chlorine dioxide by acid. Fermentation media containing biomass hydrolysate may contain a percent of hydrolysate with one or more additional sugars and/or other added components, or the media may contain 90% or more hydrolysate with minor additions such as sorbitol, as described below. In various embodiments cellulosic biomass hydrolysate is at least about 50%, 60%, 79%, 80%, 90% or 95% of the final volume of fermentation broth. Typically about 10% of the final volume of fermentation broth is seed inoculum.

The solids content of biomass hydrolysate is typically between about 10% and 40%, depending on the pretreatment and saccharification methods employed. More typically the solids content is about 25%, with a medium containing 90% cellulosic biomass hydrolysate having about 23% solids. In one embodiment the cellulosic biomass hydrolysate fermentation medium and SCD mixture contains at least about 20% solids based on dry weight of biomass to total mixture weight.

In one embodiment SCD is added to a saccharification reaction slurry that is a source of fermentable sugars for *Zymomonas* cell fermentation. The saccharification reaction slurry may contain any biomaterial that contributes insoluble solids to the reaction such as cereal grains (such as corn, wheat, barley, and rye) and cellulosic (or lignocellulosic) biomass, making the reaction a slurry. In addition, the saccharification reaction slurry contains at least one sugar-generating enzyme such as a glucoamylase used with starch-containing biomaterials or at least one cellulase used with cellulosic biomass, as described above.

In one embodiment the present saccharification reaction slurry mixture composition comprises cellulosic biomass, at least one cellulase enzyme, and stabilized chlorine dioxide. In one embodiment the concentration of SCD is initially at least about 10 mg/kg, as described further below, with the amount of stabilized chlorine dioxide given in terms of the amount of chlorine dioxide that can be released upon complete activation of stabilized chlorine dioxide by acid. In one embodiment the mixture contains at least about 20% solids based on dry weight of biomass to total mixture weight.

SCD may be added to a saccharification reaction slurry at any time during the saccharification reaction, such as at the beginning of the reaction, end of the reaction, or anytime during the reaction. SCD may be added to a saccharification reaction slurry when hybrid sacharification and fermentation (HSF) is performed. In the HSF process, partial saccharification is achieved prior to addition of a biocatalyst, and saccharification and fermentation occur concurrently thereafter. When performing HSF, SCD is added during saccharification at a time that is sufficient to achieve the time period prior to *Zymomonas* cell inoculation that is described below.

Method for SCD Use with *Zymomonas* Fermentations

It was found herein that although *Zymomonas* cells are sensitive to chlorine dioxide, if a period of time is allowed to elapse between SCD addition to a composition for fermentation and *Zymomonas* cell inoculation of the resulting SCD mixture, the cells can grow and produce ethanol similarly to cells inoculated into a medium to which no SCD was added. The period of time allowed to elapse between SCD addition and *Zymomonas* cell inoculation depends upon multiple factors including the pH and temperature of the SCD mixture, type of composition to which SCD is added, and amount of SCD added.

The pH of the SCD mixture is below 7 to support release of chlorine dioxide, as described above. Typically the SCD mixture has a pH that is less than about 6. For example, cellulosic biomass saccharification reactions are typically performed at a pH that is between about 5 and 6, and hydrolysate medium is typically used in *Zymomonas* fermentations at a pH that is between about 5 and 6. Therefore these compositions may be used directly with SCD without further pH adjustment.

Prior to *Zymomonas* cell inoculation the temperature of the SCD mixture is maintained at greater than 33° C. The temperature may be maintained at about 34, 35, 36, 37, 38, 39, 40, 41, 42, 43, 44, 45, 46, 47, 48, 49, or 50° C., or greater. The temperature is kept below a level that is detrimental to nutrients needed for fermentation. In various embodiments the temperature of the SCD mixture is maintained at 35° C. or greater, 40° C. or greater, or about 47° C. If the SCD mixture is at a temperature that is higher than is suitable for *Zymomonas* cells, the temperature is reduced to a temperature that is suitable for *Zymomonas* cells prior to *Zymomonas* cell inoculation. Temperatures that are suitable for *Zymomonas* cells are temperatures at which *Zymomonas* cells survive, that need not be optimal for fermentation. *Zymomonas* cells may be inoculated into a mixture that is at a temperature higher than optimal for fermentation, where after the resulting fermentation broth cools to fermentation temperature. In one embodiment the temperature of the SCD mixture at inoculation is less than 40° C. In other embodiments the temperature is 37° C. or lower, 35° C. or lower, or 33° C. or lower.

When SCD is added to fermentation medium comprising cellulosic biomass hydrolysate or saccharification reaction slurry, the time period between SCD addition and *Zymomonas* cell inoculation is greater than 6 hours. In various embodiments the time period may be 7, 8, 9, 10, 11, or 12 or more hours. The specific time used with a specific type of cellulosic biomass hydrolysate medium or saccharification reaction slurry, specific dose of SCD, and specific temperature may readily be determined by one skilled in the art based on performance of the *Zymomonas* cells following inoculation as exemplified in Examples herein.

When SCD is added to a fermentation medium lacking cellulosic biomass hydrolysate, the time period between SCD addition and *Zymomonas* cell inoculation is greater than 8 hours. In various embodiments the time period may be 9, 10, 11, 12, 13, 14, 15, 16, 17, 18, 19, or 20, or more hours. The specific time used with a specific type of fermentation medium lacking cellulosic biomass hydrolysate, specific dose of SCD, and specific temperature may readily be determined by one skilled in the art based on performance of the *Zymomonas* cells following inoculation as exemplified in Examples herein.

SCD is added to a composition for fermentation in an effective amount to control contamination in the fermentation broth resulting from *Zymomonas* cell inoculation of the composition. As described above, concentrations of SCD are typically specified as the amount of chlorine dioxide ($ClO_2$) that can be released from an SCD preparation upon complete activation by acid. The concentration of $ClO_2$ that is needed to provide control of contamination in a *Zymomonas* fermentation broth will vary depending on factors such as growth and production characteristics of the *Zymomonas* strain used, the type, temperature, and pH of the composition for fermentation to which SCD is added (described above), and the initial level of contamination. Control of contaminating bacteria may be assessed by determining the level of lactic acid in a fermentation broth, where the presence of less than about 5 g/L of lactic acid even after about 40 hours of fermentation indicates that contamination is controlled. Contamination may be controlled at less than about 5 g/L of lactic acid in the fermentation broth, or less than 4 g/L or 3 g/L or 2 g/L or 1 g/L of lactic acid. The amount of lactic acid in fermentation broth is typically assayed by HPLC, as is known by one skilled in the art. An effective amount of SCD may be at least about 10, 25, 50, 75, 100, 125, 150, 175, 200, 250, 275, 300, 350 mg/kg, or more The effective amount of $ClO_2$ used with a specific composition for fermentation under specified conditions may be readily determined by one skilled in the art based on experiments described in Examples herein. For example, a concentration of about 150 mg/kg of $ClO_2$ is an effective amount used to control a 5 or 10 vol % inoculation of *L. plantarum* culture of $OD_{600}$ about 2 in hydrolysate medium under conditions described in Example 4 herein.

Inoculum of *Zymomonas* Cells

In the present method inoculating with *Zymomonas* cells produces a fermentation broth. Inoculation may be using any source of *Zymomonas* cells that is effective in starting a growing culture. Typically, *Zymomonas* cells are stored as frozen stocks, and cells are revived by growing in a small culture in defined medium. The small culture is used as an inoculum that is added to fermentation medium to produce a fermentation broth, or culture. A small culture may also be used to inoculate a seed culture. The *Zymomonas* cells are grown in the seed culture, which is then added as an inoculum to a large scale fermentation. A seed culture used as an inoculum may contain sterile medium and require no antimicrobial for contamination control. Alternatively, a seed culture used as an inoculum may contain any fermentation medium, as described above, that may be contaminated such as by process equipment or biomaterial, where SCD is used to control contamination prior to *Zymomonas* cell inoculation as described above. Inoculation is typically using 1% to 10% of the final volume of the medium that is inoculated.

*Zymomonas* Cells

Any strain of *Zymomonas* cells may be used in the present methods, and is selected based on factors including the type of medium to be used and the desired output of the fermentation process. Any strain of *Zymomonas* that is an effective biocatalyst for the desired production process may be used. For example, *Zymomonas* cells naturally produce ethanol using glucose, fructose and/or sucrose as fermentation substrates, but xylose is not metabolized. In one embodiment the *Zymomonas* cells used in the present methods and compositions have been engineered for xylose utilization, which is particularly desired when using cellulosic biomass hydrolysate as fermentation medium, which contains xylose.

Strains of ethanol-producing *Zymomonas*, such as *Z. mobilis* have been engineered for xylose fermentation to ethanol. Typically four genes have been introduced into *Z. mobilis* for expression of four enzymes involved in xylose metabolism to create a xylose utilization metabolic pathway (FIG. 1) as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol (see FIG. 1). DNA sequences encoding these enzymes may be obtained from any of numerous microorganisms that are able to metabolize xylose, such as enteric bacteria, and some yeasts and fungi. Sources for the coding regions may include

*Xanthomonas, Klebsiella, Escherichia, Rhodobacter, Flavobacterium, Acetobacter, Gluconobacter, Rhizobium, Agrobacterium, Salmonella, Pseudomonads,* and *Zymomonas*. The coding regions of *E. coli* are typically used.

The encoding DNA sequences are operably linked to promoters that are expressed in *Zymomonas* cells such as the promoter of *Z. mobilis* glyceraldehyde-3-phosphate dehydrogenase (GAP promoter), and *Z. mobilis enolase* (ENO promoter). A mutant GAP promoter with increased expression as disclosed in U.S. Pat. No. 7,989,206, which is incorporated herein by reference, is also useful for expression in *Zymomonas*. The coding regions may individually be expressed from promoters, or two or more coding regions may be joined in an operon with expression from the same promoter. The resulting chimeric genes may be introduced into *Zymomonas* cells and maintained on a plasmid, or integrated into the genome using, for example, homologous recombination, site-directed integration, or random integration. Examples of strains engineered to express a xylose utilization metabolic pathway include CP4(pZB5) (U.S. Pat. No. 5,514,583), ATCC31821/pZB5 (U.S. Pat. No. 6,566,107), 8b (US 2003/0162271; Mohagheghi et al., (2004) Biotechnol. Lett. 25; 321-325), and ZW658 (ATTCC # PTA-7858). Cells of *Zymomonas* that are engineered for expression of the xylose utilization metabolic pathway generally require a period of adaptation in xylose-containing medium prior to being able to grow in medium that contains xylose as the only sugar.

In additional embodiments the *Zymomonas* cells have one or more additional genetic modification that improves the strain such as one that increases growth rate and/or cell mass, increases utilization of xylose and/or allows use of other sugars such as arabinose, increases tolerance to inhibitory compounds such as acetate, or increases production of ethanol.

In one embodiment *Zymomonas* cells may be additionally engineered for arabinose utilization which is described in U.S. Pat. No. 5,843,760, which is incorporated herein by reference. To allow arabinose utilization, genes expressed in addition to genes of the xylose utilization pathway include: 1) L-arabinose isomerase to convert L-arabinose to L-ribulose, 2) L-ribulokinase to convert L-ribulose to L-ribulose-5-phosphate, and 3) L-ribulose-5-phosphate-4-epimerase to convert L-ribulose-5-phosphate to D-xylulose (U.S. Pat. No. 5,843,760). As disclosed in US 2011/0143408, which is incorporated herein by reference, improved arabinose utilization may be achieved by additionally expressing an arabinose-proton symporter, such as by expressing a coding region from an araE gene.

In another embodiment the endogenous himA gene, which encodes the alpha subunit of the integration host factor, is genetically modified to reduce its expression which improves growth in medium containing acetate as described in U.S. Pat. No. 7,897,396, which is incorporated herein by reference. Acetate is present in biomass hydrolysate, thus when using medium containing biomass hydrolysate, increased tolerance to this component is desired.

In another embodiment a genetic modification is made that reduces glucose-fructose oxidoreductase (GFOR) activity as described in U.S. Pat. No. 7,741,119, which is incorporated herein by reference. Reduced expression of GFOR, as well as of the himA gene, may be by any method such as those described above for reducing aldose reductase activity.

In another embodiment a genetic modification is made which increases ribose-5-phosphate isomerase (RPI) activity, as disclosed in commonly owned and co-pending U.S. patent application Ser. No. 13/161,734, which is incorporated herein by reference. Increased RPI expression may be accomplished by increasing expression of the endogenous RPI encoding gene, such as with a promoter that is more highly active than the native promoter, or by expressing a heterologous gene encoding any protein or polypeptide with ribose-5-phosphate isomerase activity in *Zymomonas*. There are two groups of ribose-5-phosphate isomerase enzymes that are called RPI-A and RPI-B, as described in U.S. application Ser. No. 13/161,734, either of which may be expressed.

In another embodiment, the xylose isomerase that is expressed as part of the xylose utilization metabolic pathway is expressed using a mutant, highly active promoter that is disclosed in U.S. Pat. No. 7,989,206 and U.S. Pat. No. 7,998,722, which are incorporated herein by reference. The mutant promoters disclosed therein are promoters of the *Zymomonas mobilis* glyceraldehyde-3-phosphate dehydrogenase gene.

In another embodiment a xylose isomerase that is expressed as part of the xylose utilization metabolic pathway is a Group I xylose isomerase included in the class of enzymes identified by EC 5.3.1.5 as disclosed in commonly owned and co-pending U.S. patent application Ser. No. 13/161,749. It is disclosed therein that Group I xylose isomerases, such as one expressed from a coding region isolated from *Actinoplanes missouriensis* (coding region with codon optimization for *Zymomonas*: SEQ ID NO:13), have higher activity in *Zymomonas* than Group 2 xylose isomerase. Group I xylose isomerases are defined therein by molecular phylogenetic bioinformatics analysis (using PHYLIP neighbor joining algorithm as implemented in PHYLIP (Phylogeny Inference Package version 3.5c; Felsenstein (1989) Cladistics 5:164-166), GroupSim analysis (Capra and Singh (2008) Bioinformatics 24: 1473-1480), and a Profile Hidden Markov Model (using the hmmsearch algorithm of the HMMER software package; Janelia Farm Research Campus, Ashburn, Va.).

In another embodiment the *Zymomonas* cells have been adapted for growth in a stress culture containing ethanol and ammonium acetate as disclosed in US Patent Application Publication 2011-0014670-A1, which is incorporated herein by reference. These *Zymomonas* strains with improved acetate tolerance are particularly useful when using cellulosic biomass hydrolysate containing fermentation medium, which contains acetate.

Strains disclosed in the above references and strains described herein provide examples of strains that may be used in the present methods and include ATCC31821/pZB5, ZW658 (ATCC #PTA-7858), ZW800, ZW801-4, ZW801-4:: ΔhimA, AcR#3, ZW705, AR3 7-321, and ZW1-XA111.

*Zymomonas* Fermentation

In the present method the fermentation medium or saccharification reaction slurry that was previously treated with SCD and then after a time period inoculated with *Zymomonas* cells, which is thus a fermentation broth, is maintained under conditions suitable for growth of the *Zymomonas* cells. In one embodiment the *Zymomonas* cells are of a strain of *Zymomonas* that is an effective biocatalyst for the production of ethanol under conditions used in fermentation, and ethanol is produced in the fermentation broth. When the sugars concentration in the fermentation medium is high such that growth is inhibited, the medium includes sorbitol, mannitol, or a mixture thereof as disclosed in commonly owned U.S. Pat. No. 7,629,156, which is incorporated herein by reference. Typically a final concentration of about 5 mM sorbitol or mannitol is present in the medium.

Typically conditions are used with temperature that is between about 30° C. and about 37° C., and with pH between about 4.5 and about 6.5. Typically cultures are incubated without supplemented air, oxygen, or other gases (which may include conditions such as anaerobic, microaerobic, or microaerophilic fermentation), for at least about 20 hours, and may be run for about 25, 30, 35, 40, 45, 50, 55, 60, 65, 70 hours or longer. Typically seed cultures are incubated for about 20 hours, while fermentation production cultures are incubated for about 40 hours or more. In order to minimize foaming, antifoam agents (any class-silicone based, organic based etc) may be added to the medium as needed.

For commercial production fermentation cultures, a variety of culture methodologies may be applied. For example, large-scale production may use both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of ethanol.

A variation on the standard batch system is the Fed-Batch system. Fed-Batch culture processes are also suitable for the present methods and compositions, and comprise a typical batch system with the exception that the substrate is added in increments as the culture progresses. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992)

The present methods may also use a continuous culture process. Continuous cultures are open systems where culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

In a production process, production fermentation cultures are typically run one after the other until a clean-out of the system is necessary.

The present methods and compositions may also be used in a hybrid saccharification and fermentation (HSF) process in which partial saccharification is carried out prior to addition of *Zymomonas* cells, then further saccharification and fermentation occur simultaneously. The second stage simultaneous saccharification and fermentation may be as described in US Patent Application Publication 2011-0318803, which is incorporated herein by reference. In this process *Zymomonas* cells are grown under conditions of low impeller agitation with high concentration of insoluble solids in a saccharification-fermentation mixture during a simultaneous saccharification and fermentation reaction for the production of high concentrations of ethanol.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "hr" means hour(s), "min" means minute(s), "sec" means second(s), "d" means day(s), "L" means liter(s), "mL" means milliliter(s), "µL" means microliter(s), "g" means grams, "µL" means microgram(s), "ng" means nanogram(s), "g/L" means grams per liter, "mM" means millimolar, "µL" means micromolar, "nm" means nanometer(s), "µmol" means micromole(s), "pmol" means picomole(s), "$OD_{600}$" means optical density measured at 600 nm, "EFT" means elapsed fermentation time, "ppm" means parts per million, "G+X" is the total of glucan and xylan in a cellulosic biomass sample.

General Methods
Strain ZW705 Description

*Zymomonas mobilis* strainZW705 was produced from strain ZW804-1. ZW801-4 is a recombinant xylose-utilizing strain of *Z. mobilis* that was described in commonly owned U.S. Pat. No. 7,741,119, which is incorporated herein by reference. Strain ZW801-4 was derived from strain ZW800, which was derived from strain ZW658, all as described in U.S. Pat. No. 7,741,119. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC 31821) via sequential transposition events, and followed by adaptation on selective media containing xylose (U.S. Pat. No. 7,629,156). ZW658 was deposited as ATCC PTA-7858. In ZW658, the gene encoding glucose-fructose oxidoreductase (gfor) was insertionally-inactivated using host-mediated, double-crossover, homologous recombination and spectinomycin resistance as a selectable marker to create ZW800 (U.S. Pat. No. 7,741,119). The spectinomycin resistance marker, which was bounded by loxP sites, was removed by site specific recombination using Cre recombinase to create ZW801-4.

Cultures of *Z. mobilis* strain ZW801-4 were adapted for growth under stress conditions of medium containing ammonium acetate to produce ZW705 as described in US Patent Application Publication 2011-0014670, which is incorporated herein by reference. A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

Strain AR3 7-31 Description

Zymomonas mobilis strain AR3 7-31 was isolated following growth of strain ZW705 in a trubidostat as described in commonly owned and co-pending U.S. patent application Ser. No. 13/316,597, which is incorporated herein by reference (also called therein Adapted 7-31). In this continuous flow culture device the concentration of ammonium acetate and ethanol was increased over time in a hydrolysate medium. The entire genome of AR3 7-31 was sequenced and compared to the sequence of the ZW705 genome. Strain AR3 7-31 was found to have a genetic modification in the zmo1432 open reading frame of the Zymomonas mobilis genome (NCBI Reference: NC_006526.2), in which zmo1432 is annotated as encoding a "fusaric acid resistance protein". Specifically, the AR3 7-31 mutation is in position 350 of the zmo1432 coding region and is a change from C to T at that position. This mutation results in a codon change for amino acid 117 from TCT to TTT resulting in a change in amino acid 117 from serine to phenylalanine. The effect of this mutation is to express a polypeptide that improves the behavior of the strain in a hydrolysate medium, increasing the strain's tolerance to various growth inhibitors in the hydrolysate and increasing the yield of ethanol.

Strain ZW1-XA111

Zymomonas mobilis strain ZW1-XA111 was prepared from strain ZW1 (ATCC 31821). ZW1 was engineered to express the four xylose utilization pathway genes: xylA, xylB, tkt, and tal as described above for ZW705. The xylA coding region was from Actinoplanes missouriensis (disclosed in US 2011/0318801, which is incorporated herein by reference) and variant high activity Z. mobilis glyceraldehyde-3-phosphate dehydrogenase gene promoters (disclosed in U.S. Pat. No. 7,989,206, which is incorporated herein by reference) were used to express xylA and a tal/tkt operon. Integration of the xylA and xylB genes inactivated the gfor locus ((U.S. Pat. No. 7,741,119, which is incorporated herein by reference). The strain was engineered for increased expression of ribose-5-phosphate isomerase (Rpi) as disclosed in commonly owned and co-pending U.S. patent application Ser. No. 13/161,734, which is incorporated herein by reference, and ribulose-phosphate 3-epimerase (Rpe) as disclosed in commonly owned and co-pending US Patent Application publication US-2013-0157331-A1, which is incorporated herein by reference. The resulting strain was passaged for 4 doublings in xylose medium for adaptation, as described in U.S. Pat. No. 7,629, 156, which is incorporated herein by reference, during which a genetic modification occurred in the zmo0976 open reading frame of the Zymomonas mobilis genome (NCBI Reference: NC_006526.2), which codes for an enzyme that has NADPH-dependent xylose reductase activity that is able to convert xylose to xylitol (Agrawal and Chen (2011) Biotechnol Lett.; online publication Jul. 1, 2011). Disruption of zmo0976 reduces NADPH-dependent xylose reductase activity by greater than 90% as disclosed in US Patent Application publication US-2013-0157332-A1, which is incorporated herein by reference, and improves growth on xylose-containing medium.

The strain was engineered to express the E. coli araBAD operon which encodes L-ribulose kinase, L-arabinose isomerase, and L-ribulose-5-phosphate-4-epimerase, respectively, which provide an arabinose assimilation pathway, in conjunction with transketolase and transaldolase activities that were introduced for xylose utilization (U.S. Pat. No. 5,843,760, which is incorporated herein by reference). Integration of an araBAD operon inactivated the pnp gene encoding polynucleotide phosphorylase thereby providing improving xylose utilization and ethanol production as disclosed in commonly owned and co-pending US Patent Application publication US-2013-0157331-A1, which is incorporated herein by reference. The resulting strain was passaged for 10 doublings in xylose medium for adaptation, as described in U.S. Pat. No. 7,629,156.

To further improve xylose utilization the strain was engineered to express a heterologous arabinose-proton symporter, encoded by the araE gene of E. coli as disclosed in US 2011/143408, which is incorporated herein by reference. The chloramphenicol resistance marked used in this step was removed from the genome producing the ZW1-XA111 strain.

Cob Composition

The amount of cellulose and xylan in starting corn cob was determined using the method ASTM E1758-01 "Standard method for the determination of carbohydrates by HPLC" as further detailed n National Renewable Energy Lagoratory (Golden, Colo.) Technical Report NREL/TP-510-42618 (revised April 2008). The composition was determined to be 34.8% cellulose, 29.2% xylan, 12.8% lignin based on dry weight.

Stover Composition

The amount of cellulose and xylan in starting stover biomas was determined by Microbac Laboratories, Inc (Boulder, Colo.). The composition was determined to be 34.8% cellulose, 21.8% xylan, 16.9% lignin based on dry weight.

Saccharification Enzymes

Accellerase® TRIO (Danisco U.S. Inc., Genencor International, Rochester, N.Y.)

Cellulase and Hemicellulase Production Strain H3A

Strain H3A is a recombinant Trichoderma reesei strain that was prepared as follows. A quad deleted T. reesei strain that was described in US2008/026376 and is a derivative of the quad deleted strain 1A52 that is described in U.S. Pat. No. 7,666,648, both references herein incorporated by reference, was co-transformed with a β-glucosidase expression cassette (CBH1 promoter, β-glucosidase) coding region, CBH1 terminator, and amdS gene), and an endoxylanase expression cassette (CBH1 promoter, endoxylanase coding region, and CBH1 terminator) using electroporation. One transformant was called strain #229. Strain #229 was co-transformed with a β-xylosidase Fv3A expression cassette (cbh1 promoter, β-xylosidase coding region, cbh1 terminator, and als gene), a β-xylosidase Fv43D expression cassette (eg1 promoter, β-xylosidase coding region, native terminator), and a Fv51A α-arabinofuranosidase expression cassette (eg1 promoter, L-α-arabinofuranosidase coding region, native terminator) using electroporation. Strain H3A was isolated from this transformation Extra-cellular protein produced during fermentation of strain H3A was separated from the cell mass by centrifugation, concentrated by membrane-ultrafiltration through a Millipore 10 kD molecular cut off weight membrane and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem 177:752). This H3A extracellular protein preparation, called herein H3A protein, was used as a combination cellulase and hemicellulase preparation effecting complex carbohydrate hydrolysis.

Cob Hydrolysate FRF10

Pretreatment

Corn cob was pretreated prior to enzymatic hydrolysis using low ammonia methods described in U.S. Pat. No. 7,932,063. A horizontal Littleford Day 130 L reactor vessel containing a jacket for passing steam around the body of the vessel (Littleford Day, Inc., Florence, Ky.) was used for pretreatment to generate pretreated cob named SSL24. The vessel was loaded with cob from seed corn processing (less than 1 mm in size) to reach 44 v % reactor fill on a wet cob basis (50.2 lbs; 22.77 kg). The cob was reduced to less than 1 mm in size using a large micropulverizer (Model #1SH, Serial #10019; Pulverizing Machinery Co., Summit, N.J.) with a 1.0 mm screen. A scoop of dry ice was added as needed to the cob before grinding to prevent the equipment from heating up. The main drive of the micropulverizer is a 5 h.p. motor, with a maximum rotor speed of 9,600 RPM. It has six rotating hammers, a shell, and is lined with opposing impact edges.

The cob had a wet loose bulk density of 0.396 g/cm$^3$ and 8 wt % moisture. Vacuum was applied to the vessel to reach 0.1 atm prior to introduction of a 28.9 wt % ammonium hydroxide solution (9.7 lbs; 4.4 kg) and water (17.2 lbs; 7.8 kg) near the top of the vessel to give a 6 wt % $NH_3$ relative to dry weight biomass and 60 wt % solids inside the vessel. A second and third pretreatment batch, named SSL25 and SSL26, were performed in the same manner to generate enough material for the subsequent saccharification. In all batches, the reactor agitator was set to 70 rpm and steam was passed through the jacket of the vessel. When the vessel reached an internal temperature of 80° C. steam was introduced near the top of the vessel to raise the internal vessel temperature to 145° C. This temperature was held for 20 minutes. At 15 minutes of this hold-up time the steam flow through the jacket was stopped. At the end of pretreatment, the reactor was depressurized through a vent condenser to reach atmospheric pressure. Vacuum (approximately to less than 1 atm; 101.3 kPa) was subsequently applied for 15 minutes to lower the temperature to less than 60° C. and remove additional ammonia and water from the pretreated cob prior to opening the bottom valve of the vessel and recovering the pretreated biomass. Final wt % of solids for pretreated cob batches SSL24, SSL25, and SSL26 was 61.1%, 66.7%, and 67.8%, respectively.

Saccharification

The FRF10 hydrolysate was generated in a 200 L fermenter using a mixture of the pretreated corn cobs from SSL24, SSL 25 and SSL26 preparations, by saccharifying with the H3A enzyme system described above. A water heel (124.0 kg) was added to the fermenter and sterilized with jacket heat to 121° C., and held for 20 minutes. The water was cooled to 47° C. and the pretreated cob mixture was added through a port on the top of the tank; 21.0 kg were added at this time. The pH was adjusted to 5.3 with 1N $H_2SO_4$ and the enzyme was added. The enzyme dosage was 4.73 kg, equivalent to 14 mg of protein per g of glucan+xylan in the total cob to be added to the reactor. Over the following 12 hours, four additions of 15.5 kg cob were made to the reactor, every three hours, with the pH adjusted to 5.3 with 1N $H_2SO_4$ after each addition. The target solids loading for this run was 25 wt %. The fermenter was controlled at 47° C. and pH 5.3 for approximately 72 hours. At the end of this time period, 20 liters was drawn off for use in these experiments, and the remaining contents of the vessel were fermented. A sample of the hydrolysate was analyzed and the remainder was stored refrigerated until use. The results of the sample analysis is shown in Table 1.

TABLE 1

| End of saccharification hydrolysate properties for FRF10 | |
|---|---|
| Monomer Glucose (g/L) | 76.26 |
| Oligomer Glucose (g/L) | 7.94 |
| Monomer Xylose (g/L) | 61.59 |
| Oligomer Xylose (g/L) | 4.11 |
| Monomer Arabinose (g/L) | 5.58 |
| Oligomer Arabinose (g/L) | 2.09 |
| Lactic Acid (g/L) | 0.00 |
| Solids content (wt %) | 23.6% |

Cob Hydrolysate FRF19

Pretreatment

Corn cob was pretreated prior to enzymatic hydrolysis as described above for cob hydrolysate FRF10 except that the vessel was loaded to reach 50 v % (60.1 lbs; 27.3 kg). The cob had a wet loose bulk density of 0.420 g/cm$^3$ and 10.9 wt % moisture. 9.8 lbs (4.4 kg) of 28.9 wt % ammonium hydroxide solution was added and 18.1 lbs of water. The first sample was SSL52, and five additional samples SSL53-SSL57 were prepared in the same manner and combined. Final wt % of solids for pretreated cob batches SSL52, SSL53, SSL54, SSL55, SSL56, and SSL27 was 70.3%, 69.4%, 68.8%, 69.6%, 68.7%, and 70.6%, respectively.

Saccharification

The FRF19 hydrolysate was generated in a 200 L fermenter using a mixture of the pretreated corn cobs from SSL52 through SSL57 preparations, treated with the H3A enzyme system described above. Saccharification was as described above except that the water heel was 111.0 kg, initially 20.0 kg of pretreated cobb was added to the fermenter, and the enzyme dosage was 6.86 kg, equivalent to 16 mg of protein per g of glucan+xylan in the total cob to be added to the reactor. Over the following 12 hours, four additions of 16.0 kg cob were made to the reactor every three hours. The target solids loading for this run was 27.5 wt %. sample hydrolysate analysis is given in Table 2.

TABLE 2

| End of saccharification hydrolysate properties for FRF19 | |
|---|---|
| Glucose (g/L) | 83.6 |
| Xylose (g/L) | 75.2 |
| Arabinose (g/L) | 7.0 |
| Lactic Acid (g/L) | <0.2 |

Stover Hydrolysate Y018

Pretreatment

Corn stover was pretreated prior to enzymatic hydrolysis using low ammonia methods described in U.S. Pat. No. 7,932,063. A horizontal Eirich 340 L reactor vessel containing a jacket for passing steam around the body of the vessel was used for pretreatment to generate pretreated cob named Y018. The vessel was loaded with stover to reach 60 v % (40.8 kg). The stover was reduced to less than 1/32 inch (0.8 mm).

The stover had a wet loose bulk density of 0.200 g/cm³ and 8.0 wt % moisture. After stover was charged, vacuum was applied to the vessel to reach −0.9 barg (−90 kPag) prior to introduction of ammonium hydroxide solution to give 8 wt % NH₃ relative to dry weight biomass and 65 wt % solids inside the vessel. In all batches, the reactor agitator was set to 40 Hz (42 rpm) and steam pressure on the jacket was 3.2 barg. Once the ammonia solution was added, steam at 16 barg (1600 kPag) was added to the vessel to raise and maintain the internal vessel temperature to 140° C. This temperature was held for 30 minutes. At the end of pretreatment, the reactor was depressurized through a vent condenser to reach atmospheric pressure. Vacuum was subsequently applied to reach −0.9 barg (−90 kPag) to lower the temperature and to remove additional ammonia and water from the pretreated stover prior to opening the bottom valve of the vessel and recovering the pretreated biomass. Final wt % of solids for pretreated stover batches Y018-X, Y018-5, and Y018-10 prepared as described was 55.5%, 67.0%, and 64.4%, respectively.

Saccharification

The Y018 hydrolysate was generated in a 1000 L fermenter using a mixture of the pretreated corn stover from batches described above, treated with Accellerase® TRIO. A water heel was added to the fermenter and sterilized with jacket heat to 121° C., and held for 20 minutes. The water was cooled to 47° C. and the pretreated stover mixture was added through a port on the top of the tank; the slurry was approximately 8 wt % solids at this time. The pH was adjusted to 5.3 with 5 wt % $H_2SO_4$ and the enzyme was added. The enzyme dosage was the equivalent to 14 mg of protein per g of glucan+xylan in the total stover to be added to the reactor. Over the following 24 hours, the remaining stover was added to a target of 25 wt % solids, with the pH controlled to 5.3 with 5 wt % $H_2SO_4$. The fermenter was controlled at 47° C. and pH 5.3 for approximately 72 hours. At the end of this time period, 20 liters was drawn off for use in these experiments, and the remaining contents of the vessel were fermented. A sample of the hydrolysate was analyzed and the remainder was stored refrigerated until use. The results of the sample analysis are shown in Table 3.

TABLE 3

End of saccharification hydrolysate properties for Y018

| | |
|---|---|
| Monomer Glucose (g/L) | 63.45 |
| Oligomer Glucose (g/L) | 18.68 |
| Monomer Xylose (g/L) | 38.81 |
| Oligomer Xylose (g/L) | 16.16 |
| Monomer Arabinose (g/L) | 8.02 |
| Oligomer Arabinose (g/L) | 3.38 |
| Lactic Acid (g/L) | 0.41 |
| Solids content (wt %) | 25.0% |

HP196 Pretreated Corn Stover

Corn stover was pretreated prior to enzymatic hydrolysis using low ammonia methods described in U.S. Pat. No. 7,932,063. A horizontal Eirich 6.7 L reactor vessel containing a jacket for passing steam around the body of the vessel was used for pretreatment to generate pretreated cob named HP196. The vessel was loaded with stover to reach 70 v % reactor fill on a wet stover basis (797.5 g). The stover had been reduced to less than 1/32 inch (0.8 mm).

The stover had a wet loose bulk density of 0.170 g/cm³ and 9.43 wt % moisture. After stover was charged, vacuum was applied to the vessel to reach −0.9 barg (−90 kPag) prior to introduction of ammonium hydroxide solution to give an 8 wt % NH₃ relative to dry weight biomass and 60 wt % solids inside the vessel. In all batches, the reactor agitator was set to 20 rpm and steam pressure on the jacket was 4.1 barg (410 kPag). Once the ammonia solution was added, steam at 4.5 barg (450 kPag) was added to the vessel to get 50 wt % solids inside the vessel. The jacket steam pressure was increased and then controlled to maintain the internal vessel temperature to 140° C. This temperature was held for 20 minutes. At the end of pretreatment, the reactor was depressurized through a vent condenser to reach atmospheric pressure. Vacuum was subsequently applied to reach −0.7 barg (−70 kPag) to lower the temperature and to remove additional ammonia and water from the pretreated stover prior to opening the bottom valve of the vessel and recovering the pretreated biomass. Final wt % of solids for pretreated stover batch HP196 was 63.55%.

Media

MRS=10 g/L peptone, 8 g/L meat extract, 4 g/L yeast extract, 20 g/L glucose, 5 g/L sodium acetate trihydrate, 1 g/L Tween 80, 2 g/L $K_2HPO_4$, 2 g/L triammonium citrate, 0.2 g/L $MgSO_4*7H_2O$, 0.05 g/L $MnSO_4*4H_2O$, pH 6.2

MRM3G10 contains per liter: yeast extract (10 g), $KH_2PO_4$ (2 g) and $MgSO_4.7H_2O$ (1 g), glucose (100 g), pH 5.5

MRM3G6 contains per liter: yeast extract (10 g), $KH_2PO_4$ (2 g) and $MgSO_4.7H_2O$ (1 g), glucose (60 g), pH 5.5

Analytical

HPLC Analysis of Ethanol, Lactic Acid

Fermentation samples were taken at timed intervals and analyzed for EtOH, residual sugars, and other metabolic products such as acetic acid, lactic acid, and glycerol using either a Waters HPLC system (Alliance system, Waters Corp., Milford, Mass.) or an Agilent 1100 Series LC; conditions=0.6 mL/min of 0.01 N H2SO4, injection volume=5 µL, autosampler temperature=10° C., column temperature=55° C., run time=25 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Example 1

Sensitivity of *Zymomonas mobilis* to Stabilized Chlorine Dioxide

Figure 2:
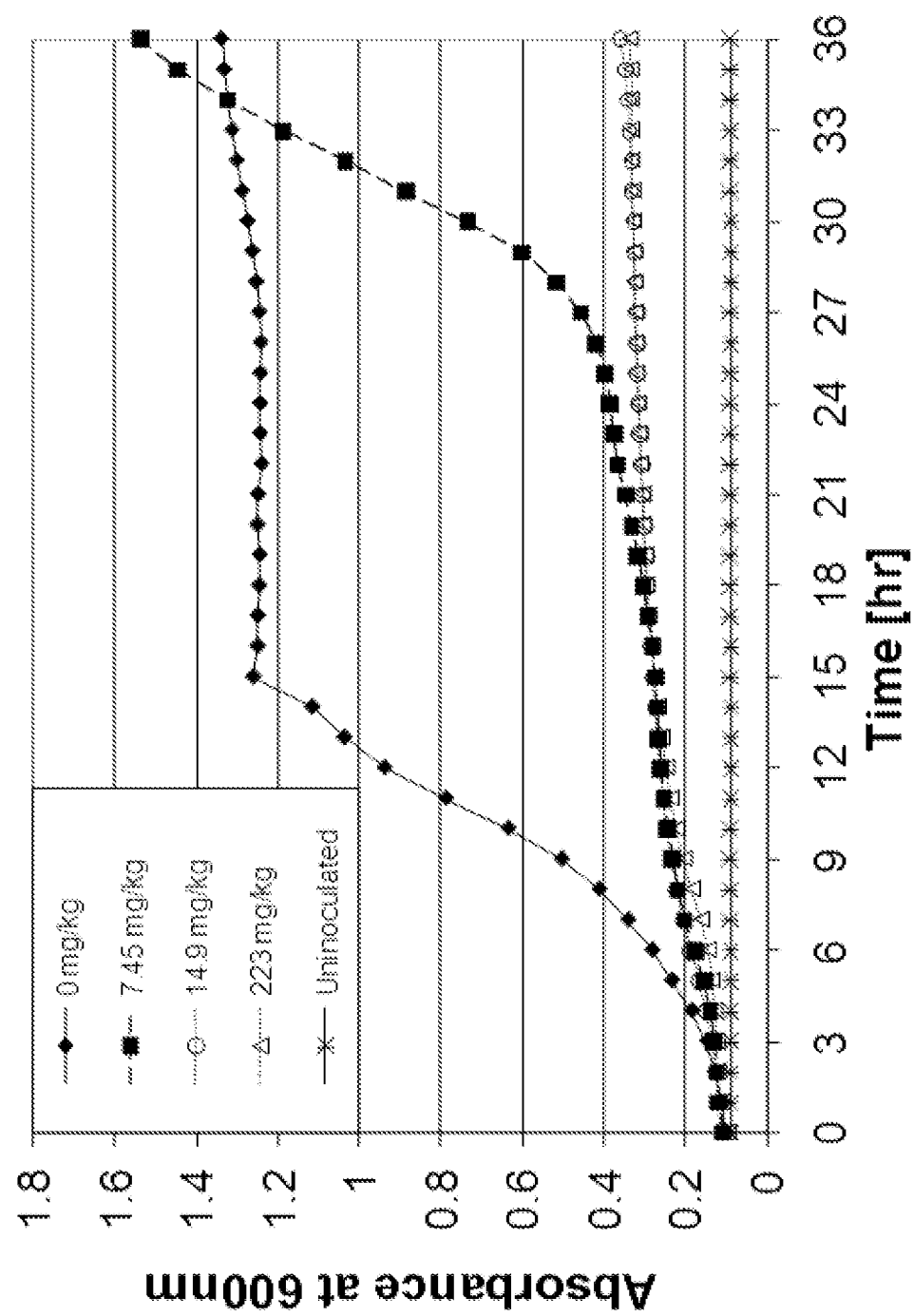
FIG. 2 is a graph showing growth of *Zymomonas* cells in MRM3G10 medium containing different amounts of stabilized chlorine dioxide (SCD).

*Z. mobilis* strain ZW705 (see General Methods) was grown as a starter culture in MRM3G10 (see General Methods). Samples of MRM3G10 medium were supplemented with stabilized chlorine dioxide (SCD) at chlorine dioxide concentrations of 0, 7.5, 15 or 224 mg/kg using a stock of FermaSure®XL (available from E. I. du Pont de Nemours and Company, Wilmington, Del.). Chlorine dioxide is given in terms of the amount of chlorine dioxide that can be released from the SCD in the FermaSure®XL solution upon complete activation by acid. The ZW705 starter culture was used to inoculate the SCD-containing medium samples, as well as a no SCD control sample, at 1% of final volume to an $OD_{600}$ of 0.1. The cultures were incubated at 32° C. and growth was monitored by $OD_{600}$. As shown in FIG. 2, the *Zymomonas* cell growth was greatly inhibited by all levels of chlorine dioxide. In 7.5 mg/kg of chlorine dioxide there was a long lag period from which cells recovered after about 27 hours and then grew similarly to the control to which no SCD was added. Cells in the samples with more chlorine dioxide did not recover during the experiment.

Example 2

Figure 3:
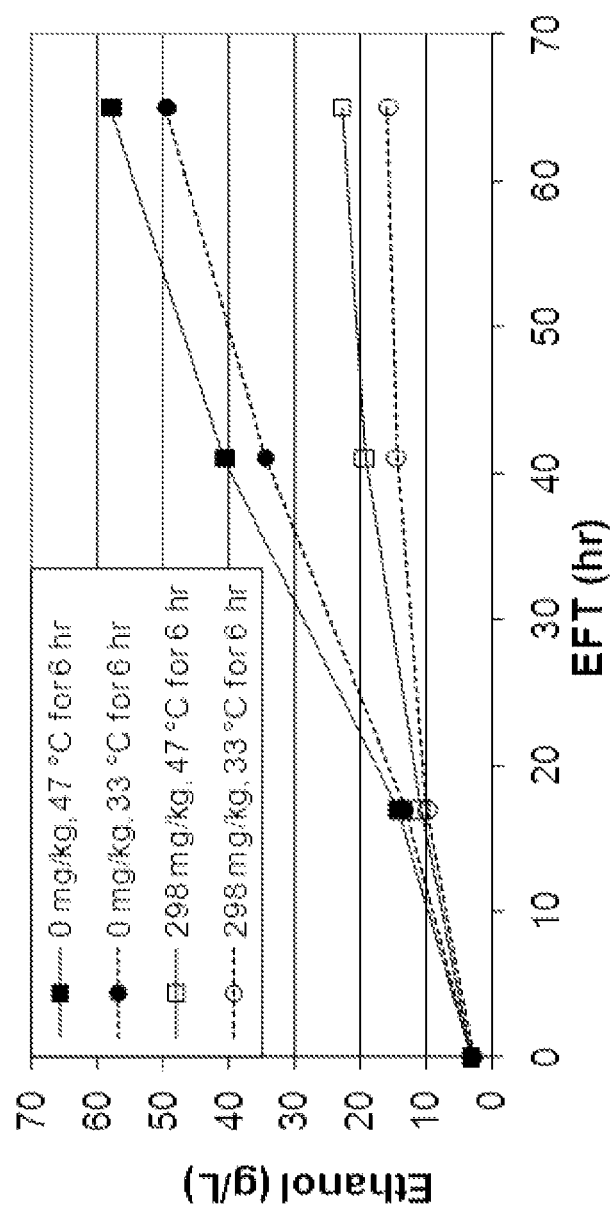
FIG. 3 is a graph showing production of ethanol by *Zymomonas* cells in hydrolysate medium which was maintained at either 33° C. or 47° C., with 298 mg/kg or no SCD added, for 6 hours prior to *Zymomonas* cell inoculation at 33° C.

Sensitivity of Zymomonas mobilis to Stabilized Chlorine Dioxide after Delayed Inoculation An experiment was performed to determine whether a lag period following SCD addition before inoculation with *Z. mobilis* cells could reduce chlorine dioxide toxicity to the cells. Chlorine dioxide was added to a concentration of 298 mg/kg in 11 mL of FRF10 corn cob hydrolysate (pH 5.3; see General Methods) using a stock of FermaSure®XL (available from E. I. du Pont de Nemours and Company, Wilmington, Del.). Chlorine dioxide is given in terms of the amount of chlorine dioxide that can be released from the SCD in the FermaSure®XL solution upon complete activation by acid. Water was added instead of FermaSure® XL to FRF10 corn cob hydrolysate for control samples. The hydrolysate was then incubated for 6 hr at 33° C. or 47° C. Samples were then held at 33° C. and inoculated with 10 vol % (final volume) of *Z. mobilis* AR3 7-31 (see General Methods) cell culture, that was grown in 10 g/L BBL yeast extract, 2 g/L $KH_2PO_4$, 5 g/L $MgSO_4*7H_2O$, 10 mM sorbitol, 150 g/L glucose, pH 5.5 at 33° C. and pH 5.5 (4 N $NH_4OH$ for pH control) to an $OD_{600}$ of about 10 (F0820), for a starting $OD_{600}$ of about 1. Ethanol production was monitored in the cultures by HPLC (see General Methods). FIG. 3 shows that the control samples fermented successfully containing ~50 g/L ethanol, while the samples containing 357 mg/kg of chlorine dioxide contained only ~15 g/L ethanol. Thus under these conditions a 6 hr lag period was not sufficient to obtain normal ethanol production levels from the *Zymomonas* cells.

Example 3

Sensitivity of Zymomonas mobilis to Stabilized Chlorine Dioxide after Prolonged Delayed Inoculation To examine the effect of longer lag times between SCD and cell additions, 151 mg/kg or 301 mg/kg of chlorine dioxide was added to FRF19 corn cob hydrolysate (see General Methods) +10 mM sorbitol, pH 5.8 using a stock of FermaSure®XL (available from E. I. du Pont de Nemours and Company, Wilmington, Del.). Chlorine dioxide is given in terms of the amount of chlorine dioxide that can be released from the SCD in the FermaSure®XL solution upon complete activation by acid. Samples were incubated for 24 or 48 hr at 47° C. Samples were then held at 33° C. and inoculated with 10 vol % (final volume) *Z. mobilis* AR3 7-31 (see General Methods) culture, that was grown in 10 g/L BBL yeast extract, 2 g/L $KH_2PO_4$, 5 g/L $MgSO_4*7H_2O$, 10 mM sorbitol, 150 g/L glucose, pH 5.5 at 33° C. (4 N $NH_4OH$ for pH control) to an $OD_{600}$ of about 10 (F1153), for a starting $OD_{600}$ of about 1. In a parallel control experiment 0, 151 mg/kg or 301 mg/kg of chlorine dioxide was added to FRF19 corn cob hydrolysate+10 mM sorbitol, pH 5.8, which was immediately inoculated in the same manner with *Z. mobilis* AR3 7-31. Ethanol production was monitored in the cultures by HPLC (see General Methods).

Figure 4:
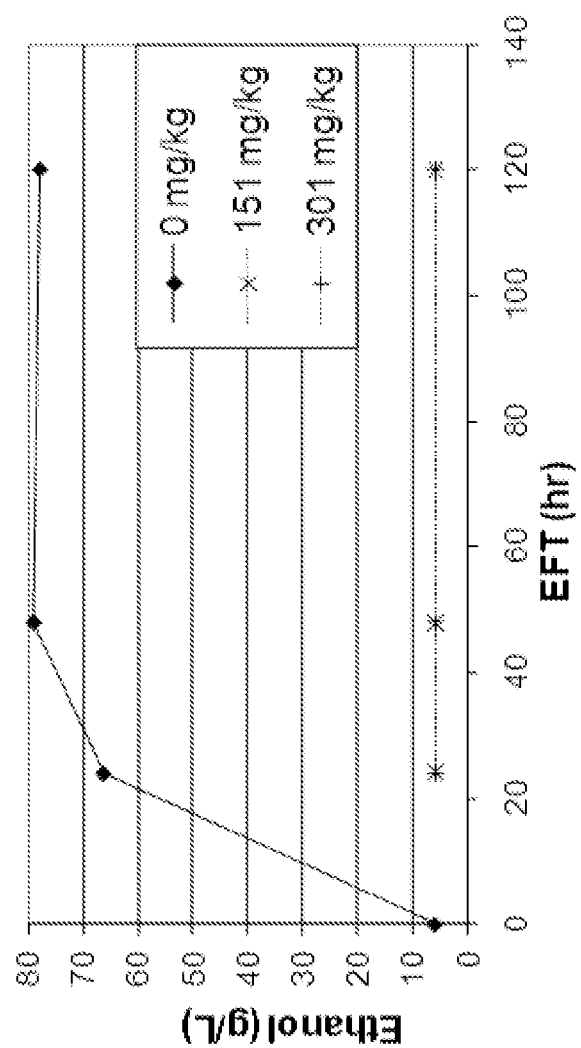
FIG. 4 shows graphs of production of ethanol by *Zymomonas* cells in hydrolysate medium that was dosed with 151 mg/kg or 301 mg/kg of chlorine dioxide and in 4(A) inoculated immediately; or in 4(B) inoculated at 33° C. after 24 or 48 hours at 47° C.
Figure 4B:
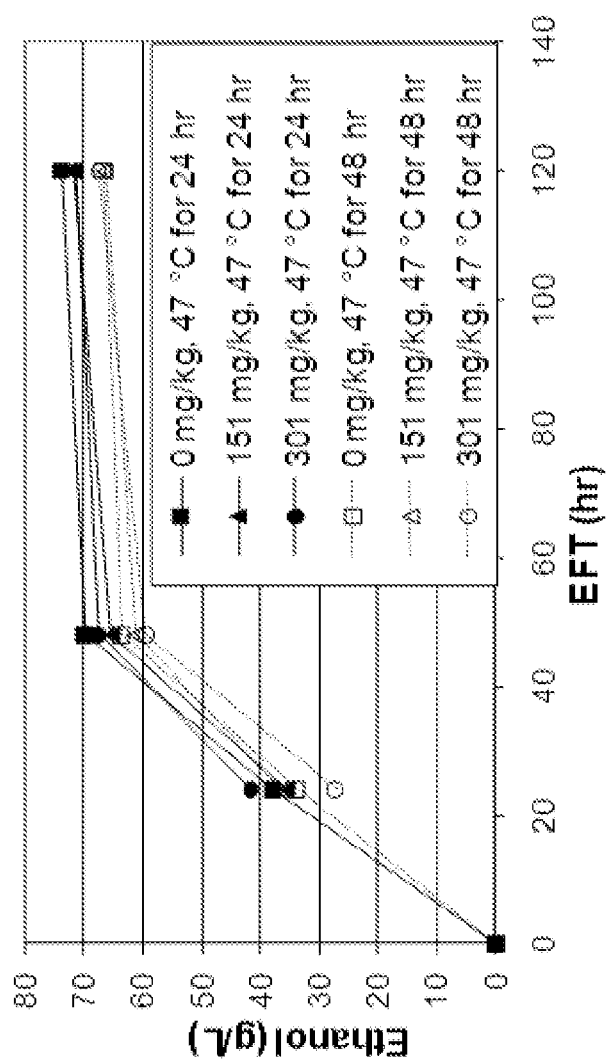

FIG. 4A shows that in cultures inoculated with *Z. mobilis* immediately after dosing with SCD, ethanol production was eliminated at either dose, while the undosed control sample contained about 80 g/L of ethanol. FIG. 4B shows that after incubation of medium containing either 151 mg/kg or 301 mg/kg of chlorine dioxide for 24 or 48 hr prior to inoculation with *Z. mobilis*, ethanol amounts were similar to amounts in the controls lacking chlorine dioxide. Thus a 24 hr time period at 47° C. in hydrolysate medium with pH of 5.5 was sufficient time between SCD addition and *Zymomonas* cell inoculation to allow normal ethanol production during *Zymomonas* fermentation.

Example 4

Control of L. plantarum in Hydrolysate Medium Using Stabilized Chlorine Dioxide

The ability of SCD to control lactic acid bacteria (LAB) that are contaminating cellulosic biomass hydrolysate was tested using *L. plantarum* strain ATCC8014 as a representative LAB contaminant. SCD was added to Y018 corn stover hydrolysate+10 mM sorbitol, pH 5.8 to a concentration of 151 mg/kg or 301 mg/kg of chlorine dioxide using a stock of FermaSure® XL. Chlorine dioxide is given in terms of the amount of chlorine dioxide that can be released from the SCD in the FermaSure®XL solution upon complete activation by acid. Samples of these media were then held at 33° C. and inoculated with 10 or 5 vol % (final volume) *L. plantarum* ATCC8014 that was harvested from a culture grown in MRS medium at 33° C., to $OD_{600}$ of about 2. There was no delay before inoculation for any of the samples. The culture medium was assayed for lactic acid content at 0, 24 and 48 hr EFT by HPLC (see General Methods). The results are given in Table 4. After 48 hr, cultures to which SCD was added had 1 g/L or less of lactic acid formation at either inoculation dose, while the control cultures without SCD produced >7 g/L lactic acid. These results show that chlorine dioxide is able to prevent lactic acid formation by a common contaminant in cellulosic hydrolysate.

TABLE 4

Lactic acid production in hydrolysate medium

| Chlorine dioxide | | | Lactic acid g/L | | |
|---|---|---|---|---|---|
| mg/kg | Inoc. vol | temp ° C. | 0 EFT | 24 EFT | 48 EFT |
| 0 | none** | 33 | 0.000 | 0.000 | 0.000 |
| 0 | 1 ml | 33 | 0.371 | 5.825 | 11.347 |
| 151 | 1 ml | 33 | 0.322 | 0.766 | 1.000 |
| 301 | 1 ml | 33 | 0.319 | 0.000 | 0.000 |
| 0 | 0.5 ml* | 33 | 0.000 | 2.598 | 7.279 |
| 151 | 0.5 ml* | 33 | 0.000 | 0.497 | 0.673 |
| 301 | 0.5 ml* | 33 | 0.000 | 0.000 | 0.000 |

**1 ml Sterile water added
*0.5 ml of culture and 0.5 ml of water added

Example 5

Effect of SCD Treatment During Saccharification Followed by Z. mobilis Fermentation The effectiveness of using SCD to control contamination during *Zymomonas* fermentation, by SCD addition during sacharification to produce hydrolysate used in fermentation, was tested. Pretreated corn stover (sample HP196; see General Methods) was autoclaved. Raw corn stover was then added to the autoclaved pretreated stover at 1% of the total weight of the pretreated stover.

Saccharification was performed using the following conditions: 47° C., initial pH 5.3, fed-batch to 25% solids, 12 mg Accellerase® TRIO/g G+X. Two saccharifications that contained the 1% raw stover biomass were run. The raw stover contains naturally-occurring contaminants. To one run SCD was added at the beginning of the saccharification, and no SCD was added to the other run. SCD was added to the saccharification mixture to a concentration of 316 mg/kg of chlorine dioxide using a stock of FermaSure® XL. Chlorine dioxide is given in terms of the amount of chlorine dioxide that can be released from the SCD in the FermaSure®XL solution upon complete activation by acid.

After 48 hr of saccharification, samples of the produced hydrolysates from both saccharification runs were taken for lactic acid analysis, then the pH of the hydrolysates was adjusted to 5.8, temperature lowered to 33° C., and 10 vol % (final volume) of a Z. mobilis strain ZW1-X111 (see General Methods) culture was added. The ZW1-X111 culture used for inoculation had been grown to $OD_{600}$ of about 12.9 in 10 g/L BBL yeast extract, 2 g/L $KH_2PO_4$, 5 g/L $MgSO_4*7H_2O$, 10 mM sorbitol, 150 g/L glucose, pH 5.5 at 33° C. and pH 5.5 (4 N $NH_4OH$ for pH control). Fermentation continued at 33° C. and the medium was assayed for ethanol after 24 hr.

At the end of saccharification (48 hr saccharification samples), the hydrolysate from the saccharification run with no SCD added contained 1.6 g/L lactic acid. The hydrolysate from the saccharification run with SCD added had no detectable lactic acid indicating control of contaminating bacteria. Fermentation in the hydrolysate to which SCD had been added reached about 36.09 g/L ethanol at 24 hr indicating a positive fermentation. Fermentation in the hydrolysate having no SCD addition contained about 34.95 g/L of ethanol.

Example 6

Lower Dose SCD Treatment During Saccharification Followed by Z. mobilis Fermentation Saccharification was performed as in Example 5 using pretreated corn stover (sample YT08-P-2; see General Methods) mixed with 1% raw corn stover. SCD was added at the beginning of separate saccharification runs to concentrations of 0, 40, 79, 119, 158, or 316 mg/kg of chlorine dioxide using a stock of FermaSure® XL. Chlorine dioxide is given in terms of the amount of chlorine dioxide that can be released from the SCD in the FermaSure®XL solution upon complete activation by acid. In a separate saccharification run, 316 mg/kg of chlorine dioxide was added after 24 hr the start of saccharification. After 48 hr of saccharification the pH of the produced hydrolysates was adjusted to 5.8, temperature lowered to 33° C., and 10 vol % (final volume) of Z. mobilis strain AR3 7-31 culture, grown to OD600 of about 1.4 in 10 g/L BBL yeast extract, 2 g/L$KH_2PO_4$, 5 g/L $MgSO_4*7H_2O$, 10 mM sorbitol, 150 g/L glucose, pH 5.5 at 33° C. and pH 5.5 (4 N $NH_4OH$ for pH control) was added. Then samples of the produced hydrolysates were taken for lactic acid analysis that are 0 time samples for fermentation (in FIG. 5). Fermentation and saccharification continued at 33° C. and the medium was assayed for ethanol after 24 hr.

Figure 5A:
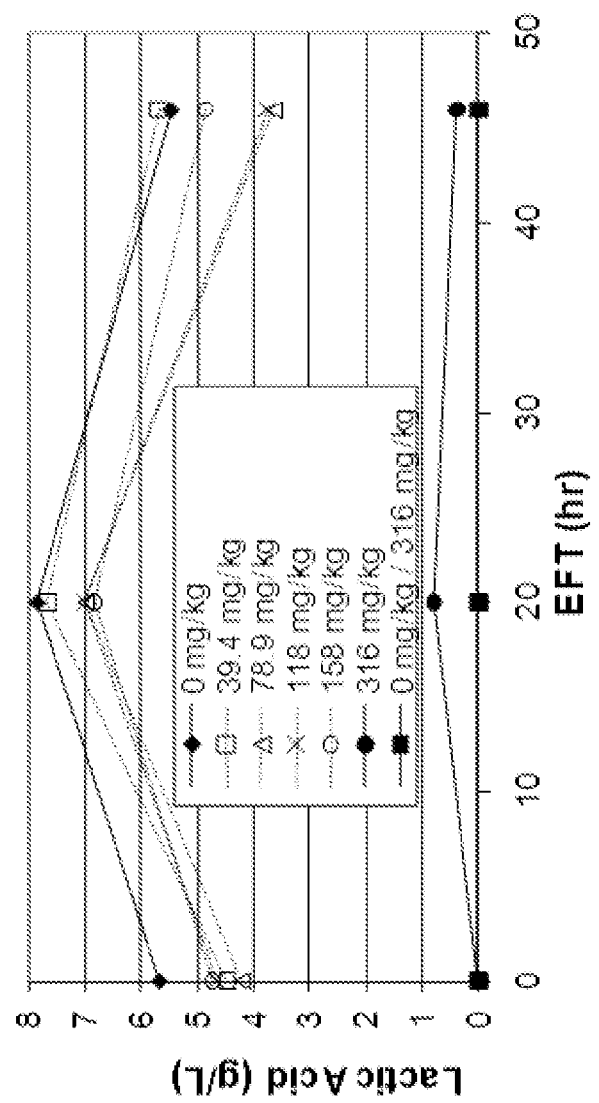
FIG. 5 shows graphs of lactic acid production (A) and ethanol production (B) by *Zymomonas* cells that were inoculated into hydrolysate that was produced from saccharification reactions to which varying amounts of SCD were added at the beginning of saccharification, with inoculation at 33° C. after 48 hours at 47° C., initial pH 5.3. In an additional sample 316 mg/kg of SCD was added after 24 hours of saccharification, followed by inoculation at 33° C. after 48 hours at 47° C.
Figure 5B:
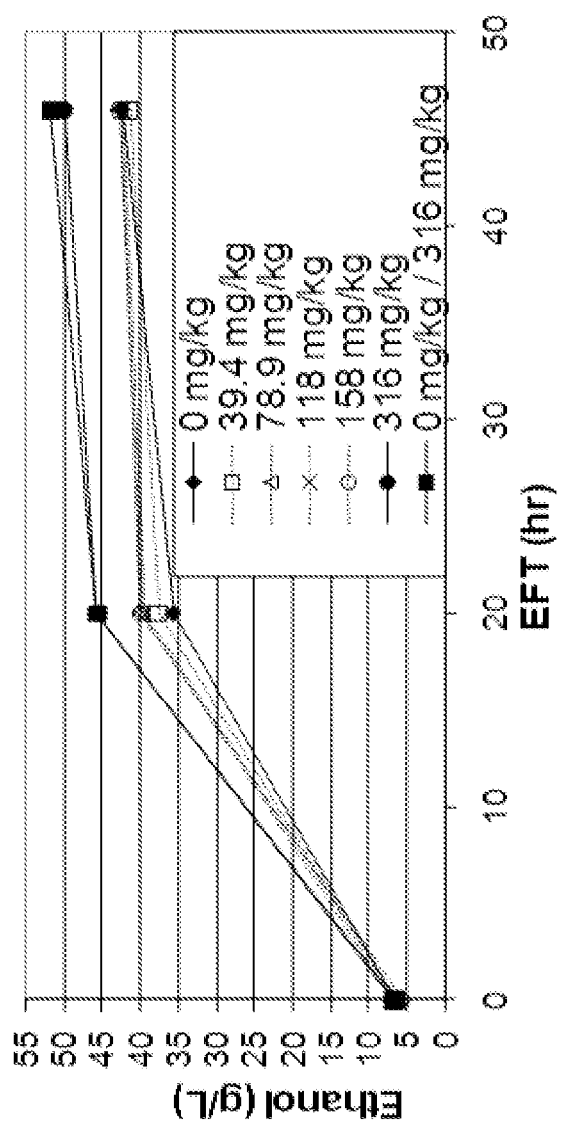

At the 0 fermentation time point (after 48 hr of saccharification), the hydrolysate with no SCD contained almost 6 g/L lactic acid as shown in FIG. 5A. At the same time point the hydrolysates to which was added 158 mg/kg or less chlorine dioxide all had small reductions in the formation of lactic acid; between 4 and 5 g/L was produced. In the hydrolysate to which was added 316 mg/kg chlorine dioxide the formation of lactic acid was reduced to <1 g/L at the 0 time point, and remained less than 1 g/L throughout the fermentation. The SCD treatment was effective at the 316 mg/kg chlorine dioxide level when added either at the beginning of saccharification, or after 24 hr (0/316 mg/kg sample in FIGS. 5 A and B) of saccharification. Both of these fermentations contained >50 g/L ethanol after 45 hr (FIG. 5B). Fermentations using hydrolysates produced with less SCD added to the saccharifications had reduced ethanol production (FIG. 5B).

Example 7

Sensitivity of Zymomonas mobilis to Stabilized Chlorine Dioxide after Prolonged Delayed Inoculation To examine the effect of longer lag times between SCD and cell additions, 301 mg/kg of chlorine dioxide was added to Y018 corn stover hydrolysate (see General Methods) +10 mM sorbitol, pH 5.8 or to MRM3G6 medium using a stock of FermaSure®XL (available from E. I. du Pont de Nemours and Company, Wilmington, Del.). Chlorine dioxide is given in terms of the amount of chlorine dioxide that can be released from the SCD in the FermaSure®XL solution upon complete activation by acid. Samples were incubated for various times at 33° C. or 47° C. Samples were then brought to 33° C. and either inoculated with 10 vol % (final volume) Z. mobilis ZW1-XA111 (see General Methods) culture that was grown in 10 g/L BBL yeast extract, 2 g/L $KH_2PO_4$, 1 g/L $MgSO_4*7H_2O$, 10 mM sorbitol, 150 g/L glucose, pH 5.5 at 33° C. (4 N $NH_4OH$ for pH control) to an $OD_{600}$ of about 10 (F1360), for a starting $OD_{600}$ of about 1 (for the 33° C. incubation experiments) or inoculated with 10 vol % (final volume) Z. mobilis AR3 7-31, that was grown in 10 g/L BBL yeast extract, 2 g/L $KH_2PO_4$, 1 g/L $MgSO_4*7H_2O$, 60 g/L glucose, pH 5.5 at 33° C. to an $OD_{600}$ of about 2.5, for a starting $OD_{600}$ of about 0.3 (for the 47° C. incubation experiments). Ethanol production was monitored in the cultures by HPLC (see General Methods).

Figure 6:
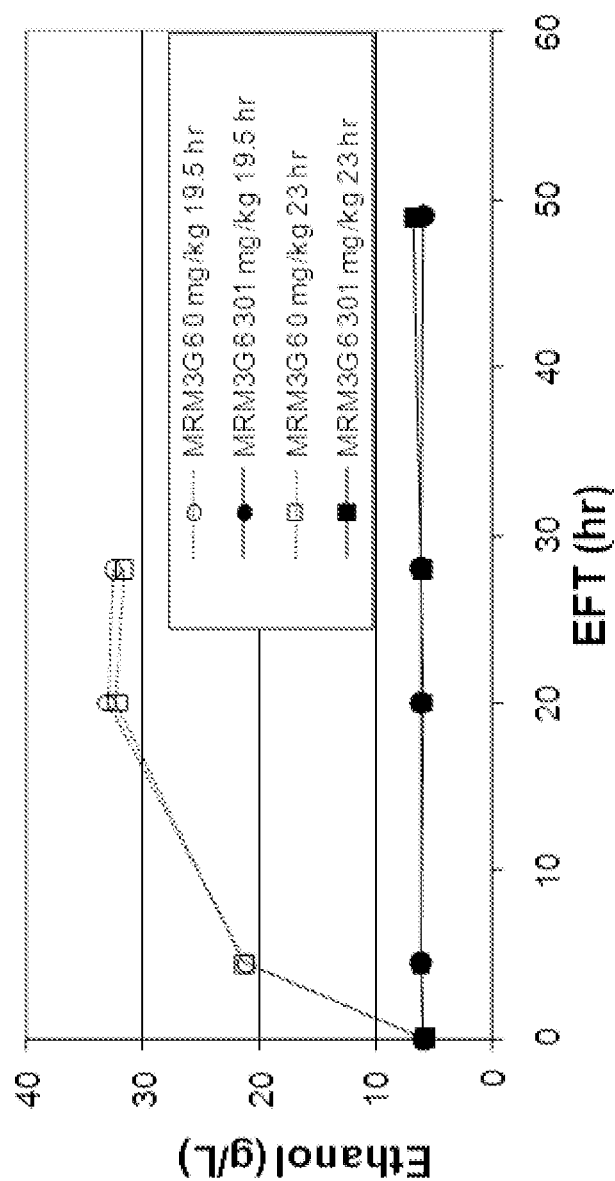
FIG. 6 shows graphs of production of ethanol by *Zymomonas* cells in MRM3G6 medium that was dosed with 301 mg/kg of chlorine dioxide and held at 33° C., then inoculated after either 19.5 or 23 hours.

FIG. 6 shows that in MRM3G6 medium, inoculation after 19.5 and 23 hr of incubation with SCD at 33° C. resulted in complete inhibition of ethanol formation while undosed controls contained greater than 30 g/L at 20 hours.

Figure 7A:
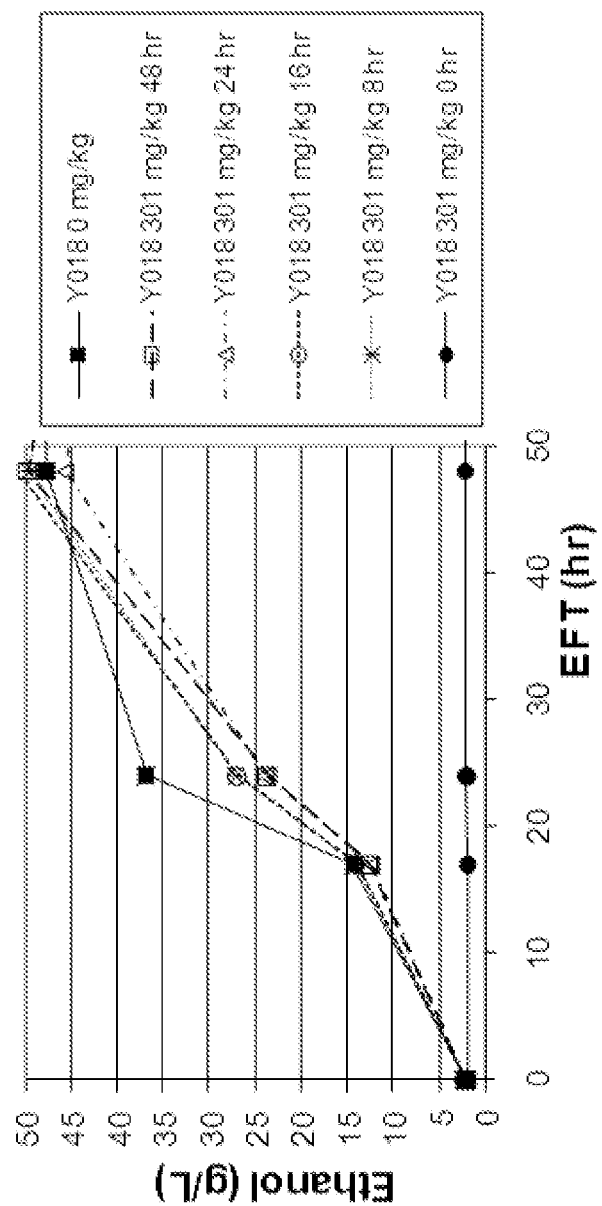
FIG. 7 shows graphs of production of ethanol by *Zymomonas* cells in medium that was dosed with 301 mg/kg of chlorine dioxide and held at 47° C. then inoculated at 33° C. after 8, 16, 24 or 48 hours, where (A) is hydrolysate medium and (B) is MRM3G6 medium.
Figure 7B:
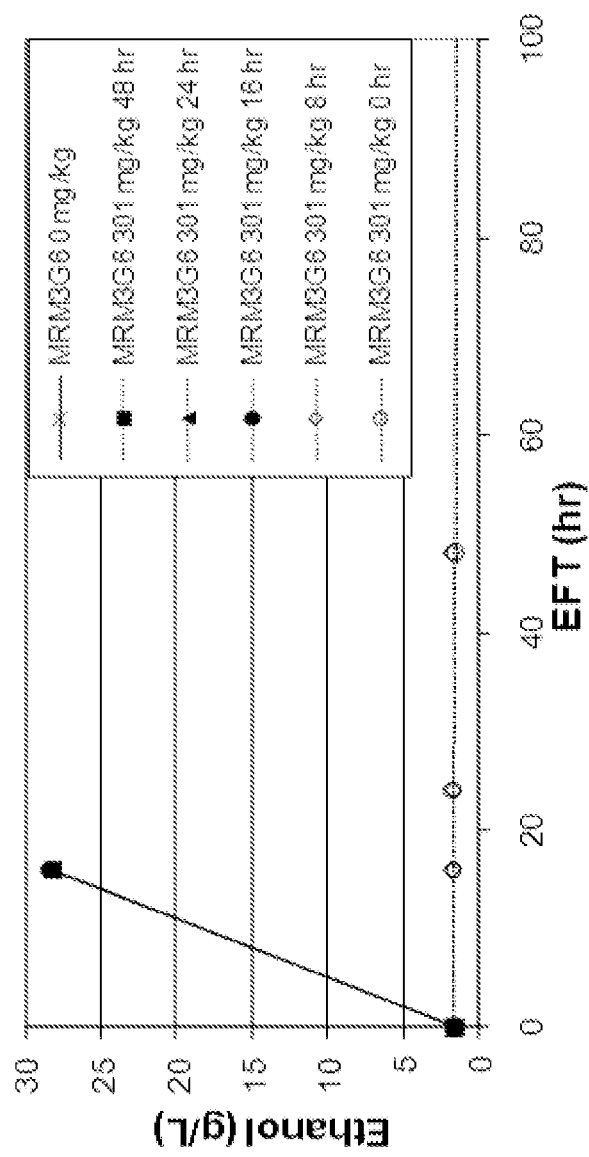

FIG. 7A shows that, at 47° C., in Y018 corn stover hydrolysate, inoculation after 8 hr of incubation with SCD allowed ethanol production levels similar to production levels in undosed controls and samples with longer incubation times prior to inoculation, indicating that 8 hr at 47° C. was a sufficient delay time period for the medium to be permissable for Z. mobilis fermentation. When using MRM3G6 medium, inoculation after 16 hr of incubation with SCD at 47° C. was sufficient to allow ethanol production levels similar to production levels in undosed controls and samples with longer incubation times prior to inoculation (FIG. 7B). Samples with inoculation after 8 hr and 0 hr incubation (immediate dose) did not contain any ethanol.

What is claimed is:
1. A composition comprising:
    a) fermentation medium comprising cellulosic biomass hydrolysate;
    b) stabilized chlorine dioxide; and
    c) Zymomonas cells.
2. A composition comprising:
    a) cellulosic biomass;
    b) at least one cellulase enzyme;

c) stabilized chlorine dioxide;
d) fermentation medium; and
e) *Zymomonas* cells.

3. The composition of claim 1 or 2, wherein the concentration of the stabilized chlorine dioxide is initially at least 10 mg/kg±10%, with the amount of the stabilized chlorine dioxide given in terms of the amount of chlorine dioxide that can be released upon complete activation of the stabilized chlorine dioxide by acid.

4. The composition of claim 1 or 2, wherein the composition contains at least 10% solids based on dry weight of biomass to total composition weight.

5. The composition of claim 1 or 2, wherein the cellulosic biomass is selected from the group consisting of corn cobs, corn husks, corn stover, grasses, wheat, wheat straw, barley straw, hay, rice straw, switchgrass, waste paper, sugar cane bagasse, sorghum, and woody plant cellulosic components.

6. The composition of claim 1, wherein the cellulosic biomass hydrolysate comprises at least one cellulase enzyme.

7. The composition of claim 1 or 2, wherein the *Zymomonas* cells are *Zymomonas mobilis* cells.

8. The composition of claim 1 or 2, wherein the composition further comprises ethanol.

9. The composition of claim 1 or 2, wherein the composition comprises less than 1 g/L of lactic acid.

10. The composition of claim 4, wherein the composition contains at least 20% solids based on dry weight of biomass to total composition weight.

\* \* \* \* \*